(12) United States Patent
Wei et al.

(10) Patent No.: US 7,320,869 B2
(45) Date of Patent: Jan. 22, 2008

(54) ANTIBODIES TO CHEMOKINE ALPHA-5

(75) Inventors: Ying-Fei Wei, Berkeley, CA (US); Yi Li, Sunnyvale, CA (US); Jian Ni, Germantown, MD (US); Craig A. Rosen, Laytonsville, MD (US); Steven M. Ruben, Brookeville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 158 days.

(21) Appl. No.: 11/224,076

(22) Filed: Sep. 13, 2005

(65) Prior Publication Data

US 2006/0008882 A1 Jan. 12, 2006

Related U.S. Application Data

(62) Division of application No. 10/114,482, filed on Apr. 3, 2002, now Pat. No. 7,060,261, which is a division of application No. 09/195,106, filed on Nov. 18, 1998, now Pat. No. 6,395,514.

(60) Provisional application No. 60/066,369, filed on Nov. 21, 1997.

(51) Int. Cl.
  *G01N 33/53* (2006.01)
  *C12N 5/12* (2006.01)
  *C07K 16/24* (2006.01)
(52) U.S. Cl. .................. 435/7.1; 435/326; 530/387.1; 530/387.9; 530/388.1; 530/387.3
(58) Field of Classification Search ............... None
  See application file for complete search history.

(56) References Cited

U.S. PATENT DOCUMENTS

| | | | |
|---|---|---|---|
| 6,319,675 B1 | 11/2001 | Briskin et al. | |
| 6,395,514 B1 | 5/2002 | Wei et al. | |
| 2002/0090657 A1 | 7/2002 | Briskin et al. | |
| 2003/0165995 A1 | 9/2003 | Briskin et al. | |
| 2004/0170628 A1 | 9/2004 | Lillard et al. | |

FOREIGN PATENT DOCUMENTS

| WO | WO-99/61471 A2 | 12/1999 |
|---|---|---|
| WO | WO-01/37872 A1 | 5/2001 |
| WO | WO-01/38874 A1 | 5/2001 |

OTHER PUBLICATIONS

Genbank Accession No. AA366329; Adams et al, "Initial assessment of human gene diversity and expression patterns based upon 83 million nucleotides of cDNA sequence," Nature 377 (6547 Suppl):3-174 (1995).
Chandrasekar et al., "CXCL16 signals via Gi, phosphatidylinositol 3-kinase, Akt, I kappa B kinase, and nuclear factor-kappa B and induces cell-cell adhesion and aortic smooth muscle cell proliferation," J Biol Chem. 279(5):3188-96 (2004).
Claverie, J.M. and Makalowski, W. "Alu Alert," Nature 371 (6500), 752 (1994).
Claverie, J.M., "Identifying coding exons by similarity search alu-derived and other potentially misleading protein sequences," Genomics 12 (4), 838-841 (1992).
Gonzalo et al, "Mouse EotaxinExpression Parallels Eosinophil Accumulation during Lung Allergic Inflammation but it is not restricted to a Th2-Type Response," Immunity. 4:1-14 (1996).
U.S. Appl. No. 09/912,293, Rosen et al.
Fukumoto et al., "Critical roles of CXC chemokine ligand 16/scavenger receptor that binds phosphatidylserine and oxidized lipoprotein in the pathogenesis of both acute and adoptive transfer experimental autoimmune encephalomyelitis," J. Immunol. 173:1620-27 (2004).
Harlow et al. Antibodies A Laboratory Manual, Cold Spring Harbor Laboratory, Ch. 5, p. 76 (1988).
Genbank Accession No. AA147076; Hillier et al., "Generation and analysis of 280,000 human expressed sequence tags," Genome Res. 6 (9): 807-828 (1996).
Genbank Accession No. AA130776; Hillier et al, "Generation and analysis of 280,000 human expressed sequence tags," Genome Res. 6(9):807-828 (1996).
Genbank Accession No. AA290712; Hillier et al, "Generation and analysis of 280,000 human expressed sequence tags," Genome Res. 6(9):807-828 (1996).
Genbank Accession No. AA121716; Hillier, L. et al, "Generation and analysis of 280,000 human expressed sequence tags," Genome Res. 6 (9): 807-828 (1996).
Genbank Accession No. AA146672; Hillier et al, "Generation and analysis of 280,000 human expressed sequence tags," Genome Res. 6 (9): 807-828 (1996).
Genbank Accession No. AA149359; Hillier et al, "Generation and analysis of 280,000 human expressed sequence tags," Genome Res. 6 (9): 807-828 (1996).
Genbank Accession No. AA411655; Hillier et al., WashU-Merck EST Project (1997).
Genbank Accession No. AA121717; Hillier et al., Generation and analysis of 280,000 human expressed sequence tags, Genome Res. 6 (9): 807-828 (1996).

(Continued)

*Primary Examiner*—Prema Mertz
(74) *Attorney, Agent, or Firm*—Foley & Lardner LLP

(57) ABSTRACT

The present invention relates to a novel CKα-5 protein which is a member of the alpha chemokine family. In particular, isolated nucleic acid molecules are provided encoding the human CKα-5 protein. CKα-5 polypeptides are also provided, as are vectors, host cells and recombinant methods for producing the same. Antibodies and fragments thereof that specifically bind to CKα-5 polypeptides are also disclosed, as are compositions and methods for making such antibodies. The invention further relates to screening methods for identifying agonists and antagonists of CKα-5 activity. Also provided are diagnostic methods for detecting immune system-related disorders and therapeutic methods for treating immune system-related disorders.

28 Claims, 5 Drawing Sheets

OTHER PUBLICATIONS

Genbank Accession No. AA151842; Hillier et al., "Generation and analysis of 280,000 human expressed sequence tags," Genome Res. 6 (9): 807-828 (1996).

Genbank Accession No. AA416552; Hillier et al., WashU-Merck EST Project 1997.

Genbank Accession No. AA130627; Hillier et al., Generation and analysis of 280,000 human expressed sequence tags, Genome Res. 6 (9): 807-828 1996.

Genbank Accession No. AA411656; Hillier et al., WashU-Merck EST Project 1997.

Genbank Accession No. AA119688; Hillier et al., "Generation and analysis of 280,000 human expressed sequence tags," Genome Res. 6 (9): 807-828 1996.

Genbank Accession No. AA235118; Hillier et al., Generation and analysis of 280,000 human expressed sequence tags, Genome Res. 6 (9): 807-828 1996.

Genbank Accession No. AA625220; Hillier et al., WashU-NCI human EST Project 1997.

Genbank Accession No. AI061333; Hillier et al., WashU-NCI human EST Project 1997.

Genbank Accession No. N22788; Hillier, L. et al., Generation and analysis of 280,000 human expressed sequence tags, Genome Res. 6 (9):807-828 (1996).

Jurka, J. and Milosavljevic, A, "Reconstruction and analysis of human Alu genes," J. Mol. Evol. 32 (2), 105-121 (1991).

Mikayama et al., "Molecular cloning and functional expression of a cDNA encoding glycosylation-inhibiting factor," Proc. Natl. Acad. Sci. USA 90:10056-10060 (1993).

Genbank Accession No. AI358175; NCI-CGAP, National Cancer Institute, Cancer Genome Anatomy Project (CGAP), Tumor Gene Index (1997).

Genbank Accession No. AI624569; NCI-CGAP, National Cancer Institute, Cancer Genome Anatomy Project (CGAP), Tumor Gene Index (1997).

Genbank Accession No. AA577696; NCI-CGAP, National Cancer Institute, Cancer Genome Anatomy Project (CGAP), Tumor Gene Index (1997).

Genbank Accession No. AA857255;NCI-CGAP, National Cancer Institute, Cancer Genome Anatomy Project (CGAP), Tumor Gene Index (1997).

Genbank Accession No. AI344574; NCI-CGAP, National Cancer Institute, Cancer Genome Anatomy Project (CGAP), Tumor Gene Index (1997).

Genbank Accession No. AI264137; NCI-CGAP, National Cancer Institute, Cancer Genome Anatomy Project (CGAP), Tumor Gene Index (1997).

Genbank Accession No. AI828235; NCI-CGAP, National Cancer Institute, Cancer Genome Anatomy Project (CGAP), Tumor Gene Index (1997).

Quentin, Y., "The Alu family developed through successive waves of fixation closely connected with primate lineage history," J. Mol. Evol. 27 (3), 194-202 (1998).

Rothenberg et al, "Murine eotaxin: An eosinophil chemoattractant inducible in endothelial cells and in interleukin 4-induced tumor suppression," Proc. Natl. Acad. Sci. USA 92:8960-8964 (1995).

Shimaoka et al., "Cutting edge: SR-PSOX/CXC chemokine ligand 16 mediates bacterial phagocytosis by APCs through its chemokine domain," J Immunol. 171(4):1647-51 (2003).

Shimaoka et al., "Molecular cloning of a novel scavenger receptor for oxidized low density lipoprotein, SR-PSOX, on macrophages," J Biol Chem. 275(52):40663-6 (2000).

Skolnick et al., "Structural genomics and its importance for gene function analysis," Nature Biotech., 18:283-287 (Mar. 2000).

Voet et al. Biochemistry. John Wiley & Sons, Inc., pp. 126-128 and 228-234 (1990).

Wilbanks et al., "Expression cloning of the STRL33/BONZO/ TYMSTRligand reveals elements of CC, CXC, and CX3C chemokines," J Immunol. 166(8):5145-54 (2001)###.

Wuttge et al., "CXCL 16/SR-PSOX is an interferon-gamma-regulated chemokine and scavenger receptor expressed in atherosclerotic lesions," Arterioscler Thromb Vasc Biol. 24(4):750-5 (2004).

Yamauchi et al., "Upregulation of SR-PSOX/CXCL16 and recruitment of CD8+ T cells in cardiac valves during inflammatory valvular heart disease," Arterioscler Thromb Vasc Biol. 24(2):282-7 (2004).

FIGURE 1A

```
1.      .         .         .         .         .         .
   CGGCGACTCTCTCCACCGGGCCGCCCGGGAGGCTCATGCAGCGCGGCTGGGTCCCGCGGC
61
        .         .         .         .         .         .
   GCCCGGATCGGGGAAGTGAAAGTGCCTCGGAGGAGGAGGGCCGGTCCGGCAGTGCAGCCG
121
        .         .         .         .         .         .
   CCTCACAGGTCGGCGGACGGGCCAGGCGGGCGGCCTCCTGAACCGAACCGAATCGGCTCC
181
        .         .         .         .         .         .
   TCGGGCCGTCGTCCTCCCGCCCCTCCTCGCCCGCCGCCGGAGTTTTCTTTCGGTTTCTTC
241
        .         .         .         .         .         .
   CAAGATTCCTGGCCTTCCCTCGACGGAGCCGGGCCCAGTGCGGGGGCGCAGGGCGCGGGA
301
        .         .         .         .         .         .
   GCTCCACCTCCTCGGCTTTCCCTGCGTCCAGAGGCTGGCATGGCGCGGGCCGAGTACTGA
361
        .         .         .         .         .         .
   GCGCACGGTCGGGGCACAGCAGGGCCGGTGGGTGCAGCTGGCTCGCGCCTCCTCTCCGGC
421
        .         .         .         .         .         .
   CGCCGTCTCCTCCGGTCCCCGGCGAAAGCCATTGAGACACCAGCTGGACGTCACGCGCCG
481
        .         .         .         .         .         .
   GAGCATGTCTGGGAGTCAGAGCGAGGTGGCTCCATCCCCGCAGAGTCCGCGGAGCCCCGA
541
        .         .         .         .         .         .
   GATGGGACGGGACTTGCGGCCCGGGTCCCGCGTGCTCCTGCTCCTGCTTCTGCTCCTGCT
    M  G  R  D  L  R  P  G  S  R  V  L  L  L  L  L  L  L  L  L     20
601
        .         .         .         .         .         .
   GGTGTACCTGACTCAGCCAGGCAATGGCAACGAGGGCAGCGTCACTGGAAGTTGTTATTG
    V  Y  L  T  Q  P  G  N  G  N  E  G  S  V  T  G  S  C  Y  C     40
661
        .         .         .         .         .         .
   TGGTAAAAGAATTTCTTCCGACTCCCCGCCATCGGTTCAGTTCATGAATCGTCTCCGGAA
     G  K  R  I  S  S  D  S  P  P  S  V  Q  F  M  N  R  L  R  K    60
721
        .         .         .         .         .         .
   ACACCTGAGAGCTTACCATCGGTGTCTATACTACACGAGGTTCCAGCTCCTTTCCTGGAG
     H  L  R  A  Y  H  R  C  L  Y  Y  T  R  F  Q  L  L  S  W  S    80
781
        .         .         .         .         .         .
   CGTGTGTGGAGGCAACAAGGACCCATGGGTTCAGGAATTGATGAGCTGTCTTGATCTCAA
     V  C  G  G  N  K  D  P  W  V  Q  E  L  M  S  C  L  D  L  K   100
```

FIGURE 1B

```
841
    AGAATGTGGACATGCTTACTCGGGGATTGTGGCCCACCAGAAGCATTTACTTCCTACCAG
     E  C  G  H  A  Y  S  G  I  V  A  H  Q  K  H  L  L  P  T  S      120
901
    CCCCCCAACTTCTCAGGCCTCAGAGGGGGCATCTTCAGATATCCACACCCCTGCCCAGAT
     P  P  T  S  Q  A  S  E  G  A  S  S  D  I  H  T  P  A  Q  M      140
961
    GCTCCTGTCCACCTTGCAGTCCACTCAGCGCCCCACCCTCCCAGTAGGATCACTGTCCTC
     L  L  S  T  L  Q  S  T  Q  R  P  T  L  P  V  G  S  L  S  S      160
1021
    GGACAAAGAGCTCACTCGTCCCAATGAAACCACCATTCACACTGCGGGCCACAGTCTGGC
     D  K  E  L  T  R  P  N  E  T  T  I  H  T  A  G  H  S  L  A      180
1081
    AGTTGGGCCTGAGGCTGGGGAGAACCAGAAGCAGCCGGAAAAAAATGCTGGTCCCACAGC
     V  G  P  E  A  G  E  N  Q  K  Q  P  E  K  N  A  G  P  T  A      200
1141
    CAGGACATCAGCCACAGTGCCGGTCCTGTGCCTCCTGGCCATCATCTTCATCCTCACCGC
     R  T  S  A  T  V  P  V  L  C  L  L  A  I  I  F  I  L  T  A      220
1201
    AGCCCTTTCCTATGTGCTGTGCAAGAGGAGGAGGGGGCAGTCACCGCAGTCCTCTCCAGA
     A  L  S  Y  V  L  C  K  R  R  R  G  Q  S  P  Q  S  S  P  D      240
1261
    TCTGCCGGTTCATTATATACCTGTGGCACCTGACTCTAATACCTGAGCCAAGAATGGAAG
     L  P  V  H  Y  I  P  V  A  P  D  S  N  T  *                      254
1321
    CTTGTGAGGAGACGGACTCTATGTTGCCCAGGCTGTTATGGAACTCCTGAGTCAAGTGAT
1381
    CCTCCCACCTTGGCCTCTGAAGGTGCGAGGATTATAGGCGTCACCTACCACATCCAGCCT
1441
    ACACGTATTTGTTAATATCTAACATAGGACTAACCAGCCACTGCCCTCTCTTAGGCCCCT
```

FIGURE 1C

1501
    CATTTAAAAACGGTTATACTATAAAATCTGCTTTTCACACTGGGTGATAATAACTTGGAC
1561
    AAATTCTATGTGTATTTTGTTTTGTTTTGCTTTGCTTTGTTTTGAGACGGAGTCTCGCTC
1621
    TGTCATCCAGGCTGGAGTGCAGTGGCATGATCTCGGCTCACTGCAACCCCATCTCCCAG
1681
    GTTCAAGCGATTCTCCTGCCTCCTCCTAAGTAGCTGGGACTACAGGTGCTCACCACCACA
1741
    CCCGGCTAATTTTTTGTATTTTTAGTAGAGACGGGGTTTCACCATGTTGACCAGGCTGGT
1801
    CTCGAACTCCTGACCTGGTGATCTGCCCACCCAGGCCTCCCAAAGTGCTGGGATTAAAGG
1861
    TGTGAGCCACCATGCCTGGCCCTATGTGTGTTTTTTAACTACTAAAAATTATTTTTGTAA
1921
    TGATTGAGTCTTCTTTATGGAAACAACTGGCCTCAGCCCTTGCGCCCTTACTGTGATTCC
1981
    TGGCTTCATTTTTTGCTGATGGTTCCCCCTCGTCCCAAATCTCTCTCCCAGTACACCAGT
2041
    TGTTCCTCCCCCACCTCAGCCCTCTCCTGCATCCTCCTGTACCCGCAACGAAGGCCTGGG
2101
    CTTTCCCACCCTCCCTCCTTAGCAGGTGCCGTGCTGGGACACCATACGGGTTGGTTTCAC
2161
    CTCCTCAGTCCCTTGCCTACCCCAGTGAGAGTCTGATCTTGTTTTTATTGTTATTGCTTT
2221
    TATTATTATTGCTTTTATTATCATTAAAACTCTAGTTCTTGTTTTGTCTCTCAAAAAAA
2281
    AAAAAAAAAAAAAAAAAAAAAAAAAAAA

FIGURE 2

```
CKa-5   24 LRPGSRVLLLLLLLLLVYLTQPGNGNEGSVTGSCYCGKRISSDSPPSVQF 73
              :: ....: ||||:              :....:|..:: .|:||.|.|. |
MIP1-b   1 MKLCVSAFSLLLLV.............AAFCDSVLSA.PIGSDPPTSCCF 36

CKa-5   74 MNRLRKHLRAYHRCLYYTR..........FQLLSWSVCGGNKDPWVQELM 113
              ||  |.: . .| |.          :   :: :|:: .:|||.|.:
MIP1-b  37 SYTSRKIHRNFVMDYYETSSLCSQPAVVFLTKKGRQICADPSEPWVNEYV 86

CKa-5  114 SCLDLK 119
              . |:|.
MIP1-b  87 NDLELN 92
```

Percent Similarity: 51.220     Percent Identity: 28.049

SEQUENCE LISTING

```
<160> NUMBER OF SEQ ID NOS: 22

<210> SEQ ID NO 1
<211> LENGTH: 2309
<212> TYPE: DNA
<213> ORGANISM: Homo sapiens
<220> FEATURE:
<221> NAME/KEY: CDS
<222> LOCATION: (542)..(1306)
<220> FEATURE:
<221> NAME/KEY: sig_peptide
<222> LOCATION: (542)..(622)
<220> FEATURE:
<221> NAME/KEY: mat_peptide
<222> LOCATION: (623)..(1303)

<400> SEQUENCE: 1
cggcgactct ctccaccggg ccgcccggga ggctcatgca gcgcggctgg gtcccgcggc    60
gcccggatcg gggaagtgaa agtgcctcgg aggaggaggg ccggtccggc agtgcagccg   120
cctcacaggt cggcggacgg gccaggcggg cggcctcctg aaccgaaccg aatcggctcc   180
tcgggccgtc gtcctcccgc ccctcctcgc ccgccgccgg agttttcttt cggtttcttc   240
caagattcct ggccttccct cgacggagcc gggcccagtg cggggggcgca gggcgcggga   300 gctccacctc ctcggctttc cctgcgtcca gaggctggca tggcgcgggc cgagtactga   360
gcgcacggtc ggggcacagc agggccggtg ggtgcagctg gctcgcgcct cctctccggc   420
cgccgtctcc tccggtcccc ggcgaaagcc attgagacac cagctggacg tcacgcgccg   480
gagcatgtct gggagtcaga gcgaggtggc tccatccccg cagagtccgc ggagccccga   540 g atg gga cgg gac ttg cgg ccc ggg tcc cgc gtg ctc ctg ctc ctg ctt   589
  Met Gly Arg Asp Leu Arg Pro Gly Ser Arg Val Leu Leu Leu Leu Leu
      -25               -20                  -15 ctg ctc ctg ctg gtg tac ctg act cag cca ggc aat ggc aac gag ggc   637
Leu Leu Leu Leu Val Tyr Leu Thr Gln Pro Gly Asn Gly Asn Glu Gly
    -10                -5                -1   1                 5 agc gtc act gga agt tgt tat tgt ggt aaa aga att tct tcc gac tcc   685
Ser Val Thr Gly Ser Cys Tyr Cys Gly Lys Arg Ile Ser Ser Asp Ser
                    10                  15                  20 ccg cca tcg gtt cag ttc atg aat cgt ctc cgg aaa cac ctg aga gct   733
Pro Pro Ser Val Gln Phe Met Asn Arg Leu Arg Lys His Leu Arg Ala
                25                  30                  35
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tac | cat | cgg | tgt | cta | tac | tac | acg | agg | ttc | cag | ctc | ctt | tcc | tgg | agc | 781  |
| Tyr | His | Arg | Cys | Leu | Tyr | Tyr | Thr | Arg | Phe | Gln | Leu | Leu | Ser | Trp | Ser |      |
|     |     | 40  |     |     |     |     | 45  |     |     |     |     | 50  |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtg | tgt | gga | ggc | aac | aag | gac | cca | tgg | gtt | cag | gaa | ttg | atg | agc | tgt | 829  |
| Val | Cys | Gly | Gly | Asn | Lys | Asp | Pro | Trp | Val | Gln | Glu | Leu | Met | Ser | Cys |      |
|     | 55  |     |     |     |     | 60  |     |     |     |     | 65  |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctt | gat | ctc | aaa | gaa | tgt | gga | cat | gct | tac | tcg | ggg | att | gtg | gcc | cac | 877  |
| Leu | Asp | Leu | Lys | Glu | Cys | Gly | His | Ala | Tyr | Ser | Gly | Ile | Val | Ala | His |      |
| 70  |     |     |     | 75  |     |     |     |     | 80  |     |     |     |     | 85  |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cag | aag | cat | tta | ctt | cct | acc | agc | cca | act | tct | cag | gcc | tca | gag | | 925  |
| Gln | Lys | His | Leu | Leu | Pro | Thr | Ser | Pro | Thr | Ser | Gln | Ala | Ser | Glu | |      |
|     |     |     |     | 90  |     |     |     |     | 95  |     |     |     |     | 100 | |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggg | gca | tct | tca | gat | atc | cac | acc | cct | gcc | cag | atg | ctc | ctg | tcc | acc | 973  |
| Gly | Ala | Ser | Ser | Asp | Ile | His | Thr | Pro | Ala | Gln | Met | Leu | Leu | Ser | Thr |      |
|     |     |     | 105 |     |     |     |     | 110 |     |     |     |     | 115 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttg | cag | tcc | act | cag | cgc | ccc | acc | ctc | cca | gta | gga | tca | ctg | tcc | tcg | 1021 |
| Leu | Gln | Ser | Thr | Gln | Arg | Pro | Thr | Leu | Pro | Val | Gly | Ser | Leu | Ser | Ser |      |
|     | 120 |     |     |     |     | 125 |     |     |     |     | 130 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gac | aaa | gag | ctc | act | cgt | ccc | aat | gaa | acc | acc | att | cac | act | gcg | ggc | 1069 |
| Asp | Lys | Glu | Leu | Thr | Arg | Pro | Asn | Glu | Thr | Thr | Ile | His | Thr | Ala | Gly |      |
| 135 |     |     |     |     | 140 |     |     |     |     | 145 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cac | agt | ctg | gca | gtt | ggg | cct | gag | gct | ggg | gag | aac | cag | aag | cag | ccg | 1117 |
| His | Ser | Leu | Ala | Val | Gly | Pro | Glu | Ala | Gly | Glu | Asn | Gln | Lys | Gln | Pro |      |
| 150 |     |     |     | 155 |     |     |     |     | 160 |     |     |     |     | 165 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gaa | aaa | aat | gct | ggt | ccc | aca | gcc | agg | aca | tca | gcc | aca | gtg | ccg | gtc | 1165 |
| Glu | Lys | Asn | Ala | Gly | Pro | Thr | Ala | Arg | Thr | Ser | Ala | Thr | Val | Pro | Val |      |
|     |     |     | 170 |     |     |     |     | 175 |     |     |     |     | 180 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | tgc | ctc | ctg | gcc | atc | atc | ttc | atc | ctc | acc | gca | gcc | ctt | tcc | tat | 1213 |
| Leu | Cys | Leu | Leu | Ala | Ile | Ile | Phe | Ile | Leu | Thr | Ala | Ala | Leu | Ser | Tyr |      |
|     |     | 185 |     |     |     |     | 190 |     |     |     |     | 195 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtg | ctg | tgc | aag | agg | agg | agg | ggg | cag | tca | ccg | cag | tcc | tct | cca | gat | 1261 |
| Val | Leu | Cys | Lys | Arg | Arg | Arg | Gly | Gln | Ser | Pro | Gln | Ser | Ser | Pro | Asp |      |
|     | 200 |     |     |     |     | 205 |     |     |     |     | 210 |     |     |     |     |      |

|     |     |     |     |     |     |     |     |     |     |     |     |     |     |      |
| --- | --- | --- | --- | --- | --- | --- | --- | --- | --- | --- | --- | --- | --- | ---- |
| ctg | ccg | gtt | cat | tat | ata | cct | gtg | gca | cct | gac | tct | aat | acc | tga | 1306 |
| Leu | Pro | Val | His | Tyr | Ile | Pro | Val | Ala | Pro | Asp | Ser | Asn | Thr |     |      |
| 215 |     |     |     |     | 220 |     |     |     |     | 225 |     |     |     |     |      |

| | |
|---|---|
| gccaagaatg gaagcttgtg aggagacgga ctctatgttg cccaggctgt tatggaactc | 1366 |
| ctgagtcaag tgatcctccc accttggcct ctgaaggtgc gaggattata ggcgtcacct | 1426 |
| accacatcca gcctacacgt atttgttaat atctaacata ggactaacca gccactgccc | 1486 |
| tctcttaggc ccctcattta aaaacggtta tactataaaa tctgcttttc acactgggtg | 1546 |
| ataataactt ggacaaattc tatgtgtatt ttgttttgtt ttgctttgct ttgttttgag | 1606 |
| acggagtctc gctctgtcat ccaggctgga gtgcagtggc atgatctcgg ctcactgcaa | 1666 |
| cccccatctc ccaggttcaa gcgattctcc tgcctcctcc taagtagctg ggactacagg | 1726 |
| tgctcaccac cacacccggc taattttttg tattttagt agagacgggg tttcaccatg | 1786 |
| ttgaccaggc tggtctcgaa ctcctgacct ggtgatctgc ccacccaggc tcccaaagt | 1846 |
| gctgggatta aggtgtgag ccaccatgcc tggccctatg tgtgtttttt aactactaaa | 1906 |
| aattattttt gtaatgattg agtcttcttt atggaaacaa ctggcctcag cccttgcgcc | 1966 |
| cttactgtga ttcctggctt cattttttgc tgatggttcc ccctcgtccc aaatctctct | 2026 |
| cccagtacac cagttgttcc tcccccacct cagccctctc ctgcatcctc ctgtacccgc | 2086 |
| aacgaaggcc tgggctttcc caccctccct ccttagcagg tgccgtgctg ggacaccata | 2146 |
| cgggttggtt tcacctcctc agtcccttgc ctaccccagt gagagtctga tcttgttttt | 2206 |

```
attgttattg cttttattat tattgctttt attatcatta aaactctagt tcttgttttg    2266
tctctcaaaa aaaaaaaaaa aaaaaaaaaa aaaaaaaaaa aaa                      2309
```

<210> SEQ ID NO 2
<211> LENGTH: 254
<212> TYPE: PRT
<213> ORGANISM: Homo sapiens

<400> SEQUENCE: 2

```
Met Gly Arg Asp Leu Arg Pro Gly Ser Arg Val Leu Leu Leu Leu
 1               5                  10                  15

Leu Leu Leu Leu Val Tyr Leu Thr Gln Pro Gly Asn Gly Asn Glu Gly
                20                  25                  30

Ser Val Thr Gly Ser Cys Tyr Cys Gly Lys Arg Ile Ser Ser Asp Ser
            35                  40                  45

Pro Pro Ser Val Gln Phe Met Asn Arg Leu Arg Lys His Leu Arg Ala
    50                  55                  60

Tyr His Arg Cys Leu Tyr Tyr Thr Arg Phe Gln Leu Leu Ser Trp Ser
65                  70                  75                  80

Val Cys Gly Gly Asn Lys Asp Pro Trp Val Gln Glu Leu Met Ser Cys
                85                  90                  95

Leu Asp Leu Lys Glu Cys Gly His Ala Tyr Ser Gly Ile Val Ala His
            100                 105                 110

Gln Lys His Leu Leu Pro Thr Ser Pro Pro Thr Ser Gln Ala Ser Glu
        115                 120                 125

Gly Ala Ser Ser Asp Ile His Thr Pro Ala Gln Met Leu Leu Ser Thr
    130                 135                 140

Leu Gln Ser Thr Gln Arg Pro Thr Leu Pro Val Gly Ser Leu Ser Ser
145                 150                 155                 160

Asp Lys Glu Leu Thr Arg Pro Asn Glu Thr Thr Ile His Thr Ala Gly
                165                 170                 175

His Ser Leu Ala Val Gly Pro Glu Ala Gly Glu Asn Gln Lys Gln Pro
            180                 185                 190

Glu Lys Asn Ala Gly Pro Thr Ala Arg Thr Ser Ala Thr Val Pro Val
        195                 200                 205

Leu Cys Leu Leu Ala Ile Ile Phe Ile Leu Thr Ala Ala Leu Ser Tyr
    210                 215                 220

Val Leu Cys Lys Arg Arg Arg Gly Gln Ser Pro Gln Ser Ser Pro Asp
225                 230                 235                 240

Leu Pro Val His Tyr Ile Pro Val Ala Pro Asp Ser Asn Thr
                245                 250
```

<210> SEQ ID NO 3
<211> LENGTH: 92
<212> TYPE: PRT
<213> ORGANISM: Rattus norvegicus

<400> SEQUENCE: 3

```
Met Lys Leu Cys Val Ser Ala Phe Ser Leu Leu Leu Val Ala Ala
 1               5                  10                  15

Phe Cys Asp Ser Val Leu Ser Ala Pro Ile Gly Ser Asp Pro Pro Thr
                20                  25                  30

Ser Cys Cys Phe Ser Tyr Thr Ser Arg Lys Ile His Arg Asn Phe Val
            35                  40                  45

Met Asp Tyr Tyr Glu Thr Ser Ser Leu Cys Ser Gln Pro Ala Val Val
        50                  55                  60
```

```
            Phe Leu Thr Lys Lys Gly Arg Gln Ile Cys Ala Asp Pro Ser Glu Pro
             65                  70                  75                  80

Trp Val Asn Glu Tyr Val Asn Asp Leu Glu Leu Asn
                             85                  90

<210> SEQ ID NO 4
<211> LENGTH: 321
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n equals a, t, g or c
<220> FEATURE:
<221> NAME/KEY: misc_feature
<222> LOCATION: (35)..(36)
<223> OTHER INFORMATION: n equals a, t, g or c
<220> FEATURE:
<221> NAME/KEY: misc_feature
<222> LOCATION: (39)
<223> OTHER INFORMATION: n equals a, t, g or c
<220> FEATURE:
<221> NAME/KEY: misc_feature
<222> LOCATION: (111)
<223> OTHER INFORMATION: n equals a, t, g or c
<220> FEATURE:
<221> NAME/KEY: misc_feature
<222> LOCATION: (123)
<223> OTHER INFORMATION: n equals a, t, g or c
<220> FEATURE:
<221> NAME/KEY: misc_feature
<222> LOCATION: (250)
<223> OTHER INFORMATION: n equals a, t, g or c
<220> FEATURE:
<221> NAME/KEY: misc_feature
<222> LOCATION: (254)
<223> OTHER INFORMATION: n equals a, t, g or c
<220> FEATURE:
<221> NAME/KEY: misc_feature
<222> LOCATION: (278)
<223> OTHER INFORMATION: n equals a, t, g or c
<220> FEATURE:
<221> NAME/KEY: misc_feature
<222> LOCATION: (287)
<223> OTHER INFORMATION: n equals a, t, g or c
<220> FEATURE:
<221> NAME/KEY: misc_feature
<222> LOCATION: (298)
<223> OTHER INFORMATION: n equals a, t, g or c
<220> FEATURE:
<221> NAME/KEY: misc_feature
<222> LOCATION: (305)
<223> OTHER INFORMATION: n equals a, t, g or c
<220> FEATURE:
<221> NAME/KEY: misc_feature
<222> LOCATION: (307)
<223> OTHER INFORMATION: n equals a, t, g or c

<400> SEQUENCE: 4
ggcagagacg ggactngcgg cccgggtccc gcgtnnctnc tgctcctgct tctgctcctg      60
ctggtgtacc taactcagcc aggcaatggc aacgagggca gcgtcactgg nagttgttat    120
tgnggtaaaa gaatttcttc cgactccccg ccatcggttc agttcatgaa tcgtctccgg    180
aaacacctga gaagcttacc atcggtgtct gatactacac gaggttccag ctcctttcct    240
ggagcgtgtn tggnaggcaa caaggaaccc atgggttnca ggattngat gagctgtnct     300 tgatntncaa aggaatgtgg g                                               321

<210> SEQ ID NO 5
<211> LENGTH: 361
<212> TYPE: DNA
```

```
<213> ORGANISM: Homo sapiens
<220> FEATURE:
<221> NAME/KEY: misc_feature
<222> LOCATION: (51)
<223> OTHER INFORMATION: n equals a, t, g or c
<220> FEATURE:
<221> NAME/KEY: misc_feature
<222> LOCATION: (74)
<223> OTHER INFORMATION: n equals a, t, g or c
<220> FEATURE:
<221> NAME/KEY: misc_feature
<222> LOCATION: (90)
<223> OTHER INFORMATION: n equals a, t, g or c
<220> FEATURE:
<221> NAME/KEY: misc_feature
<222> LOCATION: (119)
<223> OTHER INFORMATION: n equals a, t, g or c
<220> FEATURE:
<221> NAME/KEY: misc_feature
<222> LOCATION: (175)
<223> OTHER INFORMATION: n equals a, t, g or c
<220> FEATURE:
<221> NAME/KEY: misc_feature
<222> LOCATION: (184)
<223> OTHER INFORMATION: n equals a, t, g or c
<220> FEATURE:
<221> NAME/KEY: misc_feature
<222> LOCATION: (303)
<223> OTHER INFORMATION: n equals a, t, g or c
<220> FEATURE:
<221> NAME/KEY: misc_feature
<222> LOCATION: (326)
<223> OTHER INFORMATION: n equals a, t, g or c
<220> FEATURE:
<221> NAME/KEY: misc_feature
<222> LOCATION: (334)
<223> OTHER INFORMATION: n equals a, t, g or c
<220> FEATURE:
<221> NAME/KEY: misc_feature
<222> LOCATION: (344)
<223> OTHER INFORMATION: n equals a, t, g or c
<220> FEATURE:
<221> NAME/KEY: misc_feature
<222> LOCATION: (357)
<223> OTHER INFORMATION: n equals a, t, g or c

<400> SEQUENCE: 5
atgacactcc aaaacatggc accttggtaa ttacgaaaac agcagaaaat ntggacatgc      60
ttactcgggg attntggccc accagaagcn tttacttcct accagccccc caatttttna    120
ggcctcagag ggggcatctt ccagatatcc acacccctgc ccagatgctc ctttnccacc    180
ttgncagtcc acttcagcgc cccaccctcc cagtaggatc actgtcctcg gacaaagagc    240
tcactcgtcc caatgaaacc accatttcac actgcgggcc acagtttggg cagctgggcc    300
tgnaggctgg gggagaacca ggaagncagc cggnaaaaaa tggntggttc ccacagncag    360
g                                                                   361

<210> SEQ ID NO 6
<211> LENGTH: 183
<212> TYPE: DNA
<213> ORGANISM: Homo sapiens
<220> FEATURE:
<221> NAME/KEY: misc_feature
<222> LOCATION: (17)..(18)
<223> OTHER INFORMATION: n equals a, t, g or c
<220> FEATURE:
<221> NAME/KEY: misc_feature
<222> LOCATION: (26)
<223> OTHER INFORMATION: n equals a, t, g or c
<220> FEATURE:
<221> NAME/KEY: misc_feature
<222> LOCATION: (32)
<223> OTHER INFORMATION: n equals a, t, g or c
```

```
<220> FEATURE:
<221> NAME/KEY: misc_feature
<222> LOCATION: (77)
<223> OTHER INFORMATION: n equals a, t, g or c
<220> FEATURE:
<221> NAME/KEY: misc_feature
<222> LOCATION: (112)
<223> OTHER INFORMATION: n equals a, t, g or c
<220> FEATURE:
<221> NAME/KEY: misc_feature
<222> LOCATION: (123)
<223> OTHER INFORMATION: n equals a, t, g or c
<220> FEATURE:
<221> NAME/KEY: misc_feature
<222> LOCATION: (147)
<223> OTHER INFORMATION: n equals a, t, g or c
<220> FEATURE:
<221> NAME/KEY: misc_feature
<222> LOCATION: (157)
<223> OTHER INFORMATION: n equals a, t, g or c
<220> FEATURE:
<221> NAME/KEY: misc_feature
<222> LOCATION: (173)
<223> OTHER INFORMATION: n equals a, t, g or c

<400> SEQUENCE: 6
aggaattaat gacctgnntt aatctnaaag antgtggaca tgcttactcg gggattgtgg      60
cccaccaaaa gcatttnctt cctaccagcc ccccaatttt taaggcctca angggggcat     120
ctncagatat ccacacccct gcccagntga tcctgtncca ccttgacagt gcnacttcag    180
agg                                                                   183

<210> SEQ ID NO 7
<211> LENGTH: 334
<212> TYPE: DNA
<213> ORGANISM: Homo sapiens
<220> FEATURE:
<221> NAME/KEY: misc_feature
<222> LOCATION: (23)
<223> OTHER INFORMATION: n equals a, t, g or c
<220> FEATURE:
<221> NAME/KEY: misc_feature
<222> LOCATION: (59)
<223> OTHER INFORMATION: n equals a, t, g or c
<220> FEATURE:
<221> NAME/KEY: misc_feature
<222> LOCATION: (67)
<223> OTHER INFORMATION: n equals a, t, g or c
<220> FEATURE:
<221> NAME/KEY: misc_feature
<222> LOCATION: (126)
<223> OTHER INFORMATION: n equals a, t, g or c
<220> FEATURE:
<221> NAME/KEY: misc_feature
<222> LOCATION: (174)
<223> OTHER INFORMATION: n equals a, t, g or c
<220> FEATURE:
<221> NAME/KEY: misc_feature
<222> LOCATION: (251)
<223> OTHER INFORMATION: n equals a, t, g or c
<220> FEATURE:
<221> NAME/KEY: misc_feature
<222> LOCATION: (295)
<223> OTHER INFORMATION: n equals a, t, g or c
<220> FEATURE:
<221> NAME/KEY: misc_feature
<222> LOCATION: (308)
<223> OTHER INFORMATION: n equals a, t, g or c
<220> FEATURE:
<221> NAME/KEY: misc_feature
<222> LOCATION: (313)
<223> OTHER INFORMATION: n equals a, t, g or c
<220> FEATURE:
<221> NAME/KEY: misc_feature
<222> LOCATION: (328)
```

-continued

<223> OTHER INFORMATION: n equals a, t, g or c

<400> SEQUENCE: 7
ggcacgagct cgcgcctcct ctncggccgc cgtctcctcc ggtccccggc gaaagcatnt    60
gagacancag ctggacgtca cgcgccggag catgtctggg agtcagagcg aggtggctcc   120
atcccngcag agtccgcgga gccccgagat gggacgggac ttgcggcccg ggtnccgcgt   180
gctcctgctc ctgcttctgc ttcctgctgg tgtacctgac tcaagccagg caatgggcaa   240 acgagggca ncgtcaattg gaagttggtt aattgtggta aaaggaattt ttttnccgac   300
ttcccggnca atnggtttca agtttcantg aatc                               334

<210> SEQ ID NO 8
<211> LENGTH: 498
<212> TYPE: DNA
<213> ORGANISM: Homo sapiens
<220> FEATURE:
<221> NAME/KEY: misc_feature
<222> LOCATION: (338)
<223> OTHER INFORMATION: n equals a, t, g or c
<220> FEATURE:
<221> NAME/KEY: misc_feature
<222> LOCATION: (364)
<223> OTHER INFORMATION: n equals a, t, g or c
<220> FEATURE:
<221> NAME/KEY: misc_feature
<222> LOCATION: (370)
<223> OTHER INFORMATION: n equals a, t, g or c
<220> FEATURE:
<221> NAME/KEY: misc_feature
<222> LOCATION: (384)
<223> OTHER INFORMATION: n equals a, t, g or c
<220> FEATURE:
<221> NAME/KEY: misc_feature
<222> LOCATION: (404)
<223> OTHER INFORMATION: n equals a, t, g or c
<220> FEATURE:
<221> NAME/KEY: misc_feature
<222> LOCATION: (407)
<223> OTHER INFORMATION: n equals a, t, g or c
<220> FEATURE:
<221> NAME/KEY: misc_feature
<222> LOCATION: (409)
<223> OTHER INFORMATION: n equals a, t, g or c
<220> FEATURE:
<221> NAME/KEY: misc_feature
<222> LOCATION: (422)
<223> OTHER INFORMATION: n equals a, t, g or c
<220> FEATURE:
<221> NAME/KEY: misc_feature
<222> LOCATION: (456)
<223> OTHER INFORMATION: n equals a, t, g or c
<220> FEATURE:
<221> NAME/KEY: misc_feature
<222> LOCATION: (458)
<223> OTHER INFORMATION: n equals a, t, g or c
<220> FEATURE:
<221> NAME/KEY: misc_feature
<222> LOCATION: (475)
<223> OTHER INFORMATION: n equals a, t, g or c
<220> FEATURE:
<221> NAME/KEY: misc_feature
<222> LOCATION: (482)
<223> OTHER INFORMATION: n equals a, t, g or c
<220> FEATURE:
<221> NAME/KEY: misc_feature
<222> LOCATION: (489)
<223> OTHER INFORMATION: n equals a, t, g or c

<400> SEQUENCE: 8
aattcggcac gaggcggccc ctccttgcag gtgcctccag gaccctctct ggtccagcct    60
gaactccttc ccggctcacc gagcccatct ccgggttccg tttgctctca ttccccgaaa   120

```
cttcatgact ccgtctcacc tactggggag tttcccagtc ccaggagaaa gggctctttc      180
ttggtggcaa cttcacgcct ctggaatgag gaaggagccg gggaaggaaa gaaggccgcc      240
gcagctaaag cccaggtctc tcctccgcag ttccagcttc ctttcctgga gcgtgtgttg      300
aggcaacaag gacccatggg ttcaggaatt tgatgagntg ttttgattca aaggtgagat      360
tttncaatgn ttttaagttt gcanccaagg tttagcagtt tcanctnana ttttttttaac    420 tnagcttttc cttgggccga aatctagact tttttnanct gtccaagatt aggtngaggg     480
gncctaccna ttggccaa                                                   498
```

<210> SEQ ID NO 9
<211> LENGTH: 387
<212> TYPE: DNA
<213> ORGANISM: Homo sapiens
<220> FEATURE:
<221> NAME/KEY: misc_feature
<222> LOCATION: (376)
<223> OTHER INFORMATION: n equals a, t, g or c

<400> SEQUENCE: 9

```
ctgactcagc caggcaatgg caacgagggc agcgtcactg gaagttgtta ttgtggtaaa      60
agaatttctt ccgactcccc gccatcggtt cagttcatga atcgtctccg gaaacacctg     120
agagcttacc atcggtgtct atactacacg aggttccagc tcctttcctg gagcgtgtgt     180
ggaggcaaca aggacccatg ggttcaggaa ttgatgagct gtcttgatct caaagaatgt     240
ggacatgctt actcggggat tgtggcccac cagaaagcat ttacttccta ccaagccccc     300
caatttctca ggcctcagag ggggcatctt cagatatcca caccctgcc cagatgctcc     360 tgtccaccct tgcagtncact cagcgcc                                        387
```

<210> SEQ ID NO 10
<211> LENGTH: 406
<212> TYPE: DNA
<213> ORGANISM: Homo sapiens

<400> SEQUENCE: 10

```
ggcgaaacga ttgagacacc agctggacgt cacgcgccgg agcatgtctg ggagtcagag      60
cgaggtggct ccatcccgc agagtccgcg gacgcccgag atgggacggg acttgcggcc     120
cgggtcccgc gtgctcctgc tcctgcttct gctcctgctg gtgtacctga ctcagccagg    180
caatggcaac gagggcagcg tcactggaag ttgttattgt ggtaaaagaa tttcttccga    240
ctccccgcca tcggttcagt tcatgaatcg tctccggaaa cacctgagag cttaccatcg    300
gtgtctatac tacacgaggt tccagctcc tttcctggag cgtgtgtggg ggcaacaagg    360
acccatgggt tcaggaattg atgagctgtc ttgatctcaa agaatg                    406
```

<210> SEQ ID NO 11
<211> LENGTH: 248
<212> TYPE: DNA
<213> ORGANISM: Homo sapiens
<220> FEATURE:
<221> NAME/KEY: misc_feature
<222> LOCATION: (7)
<223> OTHER INFORMATION: n equals a, t, g or c
<220> FEATURE:
<221> NAME/KEY: misc_feature
<222> LOCATION: (25)
<223> OTHER INFORMATION: n equals a, t, g or c
<220> FEATURE:
<221> NAME/KEY: misc_feature
<222> LOCATION: (27)

<223> OTHER INFORMATION: n equals a, t, g or c
<220> FEATURE:
<221> NAME/KEY: misc_feature
<222> LOCATION: (90)
<223> OTHER INFORMATION: n equals a, t, g or c

<400> SEQUENCE: 11

| | | |
|---|---|---|
| gcttctnctc ctgctggtgt acctnantca gccaggcaat ggcaacgagg gcagcgtcac | 60 |
| tggaagttgt tattgtggta aaagaatttn ttccgactcc ccgccatcgg ttcagttcat | 120 |
| gaatcgtctc cggaaacacc tgagagctta ccatcggtgt ctatactaca cgaggttcca | 180 |
| gctcctttcc tggagcgtgt gtgggggcaa caaggaccca tgggttcagg aattgatgag | 240 |
| ctgtctttt | 248 |

<210> SEQ ID NO 12
<211> LENGTH: 425
<212> TYPE: DNA
<213> ORGANISM: Homo sapiens
<220> FEATURE:
<221> NAME/KEY: misc_feature
<222> LOCATION: (244)
<223> OTHER INFORMATION: n equals a, t, g or c
<220> FEATURE:
<221> NAME/KEY: misc_feature
<222> LOCATION: (308)
<223> OTHER INFORMATION: n equals a, t, g or c
<220> FEATURE:
<221> NAME/KEY: misc_feature
<222> LOCATION: (375)
<223> OTHER INFORMATION: n equals a, t, g or c
<220> FEATURE:
<221> NAME/KEY: misc_feature
<222> LOCATION: (423)
<223> OTHER INFORMATION: n equals a, t, g or c

<400> SEQUENCE: 12

| | | |
|---|---|---|
| ttactcgggg attgtggccc accagaagca tttacttcct accagccccc caacttctca | 60 |
| ggcctcagag ggggcatctt cagatatcca caccctgcc cagatgctcc tgtccacctt | 120 |
| gcagtccact cagcgcccca ccctcccagt aggatcactg tcctcggaca aagagctcac | 180 |
| tcgtcccaat gaaaccacca ttcacactgc gggccacagt ctggcagttg ggcctgaggc | 240 |
| tggnggagaa ccagaagcag ccggaaaaaa atgctggtcc cacagccagg acatcagcca | 300 |
| caagtgcngg tcctgtgcct cctggccatc atcttcatcc tcacccgcag ccctttccta | 360 |
| tgtgctgtga agagngagga gggggcagtc acgcagtcct tctccagatt ctggccggtt | 420 |
| canta | 425 |

<210> SEQ ID NO 13
<211> LENGTH: 209
<212> TYPE: DNA
<213> ORGANISM: Homo sapiens

<400> SEQUENCE: 13

| | | |
|---|---|---|
| tttcttccga ctccccgcca tcggttcagt tcatgaatcg tctccggaaa cacctgagag | 60 |
| cttaccatcg gtgtctatac tacacgaggt tccagctcct ttcctggagc gtgtgtggag | 120 |
| gcaacaagga cccatgggtt caggaattga tgagctgtct tgatctcaaa gaatgtggac | 180 |
| atgcttactc ggggattgtg gcccaccag | 209 |

<210> SEQ ID NO 14
<211> LENGTH: 405
<212> TYPE: DNA
<213> ORGANISM: Homo sapiens -continued

```
<220> FEATURE:
<221> NAME/KEY: misc_feature
<222> LOCATION: (159)
<223> OTHER INFORMATION: n equals a, t, g or c

<400> SEQUENCE: 14
agatatccac acccctgccc agatgctcct gtccaccttg cagtccactc agcgccccac    60
cctcccagta ggatcactgt cctcggacaa agagctcact cgtcccaatg aaaccaccat   120
tcacactgcg ggccacagtc tggcagctgg gcctgaggnt ggggagaacc agaagcagcc   180
ggaaaaaaat gctggtccca cagccaggac atcagccaca gtgccagtcc tgtgcctcct   240
ggccatcatc ttcatcctca ccgcagccct ttcctatgtg ctgtgaagat tgaggagggg   300
gcagtcaccg cagtcctctc cagatctgcc cggttcatta tatacctggt ggcacctgac   360
tctaatacct tgagccaaga atggaagctt gtgaggagac ggact                   405

<210> SEQ ID NO 15
<211> LENGTH: 27
<212> TYPE: DNA
<213> ORGANISM: Artificial sequence
<220> FEATURE:
<223> OTHER INFORMATION: Contains an NcoI restriction site

<400> SEQUENCE: 15
gcgccatgga atggcaacga gggcagc                                        27

<210> SEQ ID NO 16
<211> LENGTH: 30
<212> TYPE: DNA
<213> ORGANISM: Artificial sequence
<220> FEATURE:
<223> OTHER INFORMATION: Contains a HindIII restriction site

<400> SEQUENCE: 16
cgcaagcttt tatgtggctg atgtcctggc                                     30

<210> SEQ ID NO 17
<211> LENGTH: 24
<212> TYPE: DNA
<213> ORGANISM: Artificial sequence
<220> FEATURE:
<223> OTHER INFORMATION: Contains a BamHI restriction enzyme site and an
      efficient signal for initiation of translation in eukaryotic
      cells, as described by Kozak, M., J. Mol. Biol. 196:947-950 (1987)

<400> SEQUENCE: 17
cgcggatccg ccatcatggg acgg                                           24

<210> SEQ ID NO 18
<211> LENGTH: 27
<212> TYPE: DNA
<213> ORGANISM: Artificial sequence
<220> FEATURE:
<223> OTHER INFORMATION: Contains an XbaI restriction site

<400> SEQUENCE: 18
gcgtctagat caggtattag agtcagg                                        27

<210> SEQ ID NO 19
<211> LENGTH: 30
<212> TYPE: DNA
<213> ORGANISM: Artificial sequence
<220> FEATURE:
<223> OTHER INFORMATION: Contains an XbaI restriction site
```

<400> SEQUENCE: 19
gcgtctagat tatgtggctg atgtcctggc                                           30

<210> SEQ ID NO 20
<211> LENGTH: 489
<212> TYPE: DNA
<213> ORGANISM: Homo sapiens
<220> FEATURE:
<221> NAME/KEY: misc_feature
<222> LOCATION: (9)
<223> OTHER INFORMATION: n equals a, t, g or c
<220> FEATURE:
<221> NAME/KEY: misc_feature
<222> LOCATION: (102)
<223> OTHER INFORMATION: n equals a, t, g or c
<220> FEATURE:
<221> NAME/KEY: misc_feature
<222> LOCATION: (165)
<223> OTHER INFORMATION: n equals a, t, g or c
<220> FEATURE:
<221> NAME/KEY: misc_feature
<222> LOCATION: (212)
<223> OTHER INFORMATION: n equals a, t, g or c
<220> FEATURE:
<221> NAME/KEY: misc_feature
<222> LOCATION: (242)
<223> OTHER INFORMATION: n equals a, t, g or c
<220> FEATURE:
<221> NAME/KEY: misc_feature
<222> LOCATION: (252)
<223> OTHER INFORMATION: n equals a, t, g or c
<220> FEATURE:
<221> NAME/KEY: misc_feature
<222> LOCATION: (261)
<223> OTHER INFORMATION: n equals a, t, g or c
<220> FEATURE:
<221> NAME/KEY: misc_feature
<222> LOCATION: (272)
<223> OTHER INFORMATION: n equals a, t, g or c
<220> FEATURE:
<221> NAME/KEY: misc_feature
<222> LOCATION: (326)
<223> OTHER INFORMATION: n equals a, t, g or c
<220> FEATURE:
<221> NAME/KEY: misc_feature
<222> LOCATION: (330)
<223> OTHER INFORMATION: n equals a, t, g or c
<220> FEATURE:
<221> NAME/KEY: misc_feature
<222> LOCATION: (337)..(338)
<223> OTHER INFORMATION: n equals a, t, g or c
<220> FEATURE:
<221> NAME/KEY: misc_feature
<222> LOCATION: (340)
<223> OTHER INFORMATION: n equals a, t, g or c
<220> FEATURE:
<221> NAME/KEY: misc_feature
<222> LOCATION: (355)
<223> OTHER INFORMATION: n equals a, t, g, or c
<220> FEATURE:
<221> NAME/KEY: misc_feature
<222> LOCATION: (359)
<223> OTHER INFORMATION: n equals a, t, g or c
<220> FEATURE:
<221> NAME/KEY: misc_feature
<222> LOCATION: (361)..(362)
<223> OTHER INFORMATION: n equals a, t, g or c
<220> FEATURE:
<221> NAME/KEY: misc_feature
<222> LOCATION: (368)..(369)
<223> OTHER INFORMATION: n equals a, t, g or c
<220> FEATURE:
<221> NAME/KEY: misc_feature
<222> LOCATION: (381)
<223> OTHER INFORMATION: n equals a, t, g or c
<220> FEATURE:
<221> NAME/KEY: misc_feature

```
<222> LOCATION: (390)
<223> OTHER INFORMATION: n equals a, t, g or c
<220> FEATURE:
<221> NAME/KEY: misc_feature
<222> LOCATION: (392)
<223> OTHER INFORMATION: n equals a, t, g or c
<220> FEATURE:
<221> NAME/KEY: misc_feature
<222> LOCATION: (396)
<223> OTHER INFORMATION: n equals a, t, g or c
<220> FEATURE:
<221> NAME/KEY: misc_feature
<222> LOCATION: (411)..(415)
<223> OTHER INFORMATION: n equals a, t, g or c
<220> FEATURE:
<221> NAME/KEY: misc_feature
<222> LOCATION: (418)..(423)
<223> OTHER INFORMATION: n equals a, t, g or c
<220> FEATURE:
<221> NAME/KEY: misc_feature
<222> LOCATION: (434)..(437)
<223> OTHER INFORMATION: n equals a, t, g or c
<220> FEATURE:
<221> NAME/KEY: misc_feature
<222> LOCATION: (461)..(462)
<223> OTHER INFORMATION: n equals a, t, g or c
<220> FEATURE:
<221> NAME/KEY: misc_feature
<222> LOCATION: (470)..(471)
<223> OTHER INFORMATION: n equals a, t, g or c
<220> FEATURE:
<221> NAME/KEY: misc_feature
<222> LOCATION: (475)
<223> OTHER INFORMATION: n equals a, t, g or c
<220> FEATURE:
<221> NAME/KEY: misc_feature
<222> LOCATION: (487)
<223> OTHER INFORMATION: n equals a, t, g or c

<400> SEQUENCE: 20
attcggcana gtgaaggctg gggagaacca gaagcagccg gaaaaaaatg ctggtcccac      60
agccaggaca tcagccacag tgccagtcct gtgcctcctg gncatcatct tcatcctcac     120
cgcagcccct tcctatgtgc tgtgcaagag gaggaggggg cagtnaccgc agtcctcttc     180
cagatctgcc ggttcattat atacctgtgg gnaactgatt ctaataactg aggccaagaa     240
tnggaaggtt tnttaggaga ngggattttt tntttcccag gttttatgg gaatttctga      300 gttaaagggt tccttccaat ttgggntttn taagggnngn gggttttaa ggggngaant      360 nncaaatnna ggttaaaggg nttttttaan antttnaaaa aaggggttta nnnnatnnn      420 nnntttttg gggnnnnttt taaagggtt ttttttaaaa nngggttttn naaanggggg      480 aaaaaanna                                                             489

<210> SEQ ID NO 21
<211> LENGTH: 395
<212> TYPE: DNA
<213> ORGANISM: Homo sapiens

<400> SEQUENCE: 21 ttttttttt tttttttttt tttttttttt tttttttttt cagggggtcag tctcctttat      60 tacacttttt gtaagaataa gccacagttt accctcacaa acttccattc ttggctcagg     120
tattagagtc aggtgccaca ggtatataat gaaccggcag atctggagag gactgcggtg     180
actgccccct cctcctcttg cacagcacat aggaaagggc tgcggtgagg atgaagatga     240
tggccaggag gcacaggacc ggcactgtgg ctgatgtcct ggctgtggga ccagcatttt     300
tttccggctg cttctggttc tccccagcct caggcccaac tgccagactg tggcccgcag     360
```

```
-continued tgtgaatggt ggtttcattg ggacgagtga gctct                              395

<210> SEQ ID NO 22
<211> LENGTH: 339
<212> TYPE: DNA
<213> ORGANISM: Homo sapiens

<400> SEQUENCE: 22
ttttcagggg tcagtctcct ttattacact ttttgtaaga ataagccaca gtttaccctc    60
acaaacttcc attcttggct caggtattag agtcaggtgc cacaggtata taatgaaccg   120
gcagatctgg agaggactgc ggtgactgcc ccctcctcct cttgcacagc acataggaaa   180
gggctgcggt gaggatgaag atgatggcca ggaggacagg accggcactg tggctgattt   240
cctggctgtg ggaccagcat ttttttccgg ctgcttctgg ttctccccag cctcaggccc   300
aactgccaga ctgtggcccg cagtgtgaat ggtggtttc                          339
```

ANTIBODIES TO CHEMOKINE ALPHA-5

CROSS REFERENCE TO RELATED APPLICATIONS

This application is a divisional of U.S. application Ser. No. 10/114,482, filed Apr. 3, 2002, now U.S. Pat. No. 7,060,261 which is a divisional of U.S. application Ser. No. 09/195,106, filed Nov. 18, 1998 (now U.S. Pat. No. 6,395,514, issued May 28, 2002), which is a non-provisional of and claims benefit under 35 U.S.C. § 119(e) of U.S. Provisional Application No. 60/066,369, filed Nov. 21, 1997, which is hereby incorporated herein by reference.

FIELD OF THE INVENTION

The present invention relates to a novel human gene encoding a polypeptide which is a member of the chemokine family. More specifically, isolated nucleic acid molecules are provided encoding a human polypeptide named Chemokine Alpha-5, hereinafter referred to as "CKα-5". CKα-5 polypeptides are also provided, as are vectors, host cells and recombinant methods for producing the same. Also provided are diagnostic methods for detecting disorders related to the immune system, and therapeutic methods for treating such disorders. The invention further relates to screening methods for identifying agonists and antagonists of CKα-5 activity.

BACKGROUND OF THE INVENTION

The ability to control the migration and "trafficking" of various cell types is controlled by a subset of factors, or proteins, among which chemokines are an example.

Chemokines, also referred to as intercrine cytokines, are a subfamily of structurally and functionally related chemotactic cytokines. These molecules are usually 8-10 kd in size, however, larger membrane bound chemokine polypeptides have been identified. In general, chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the "C-X-C" therefore, referred to as the "C-C" subfamily. Thus far, at least sixteen different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein 1 (MIP-1) is able to suppress hematopoietic stem cell proliferation, platelet factor-4 (PF-4) is a potent inhibitor of endothelial cell growth, Interleukin-8 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis.

Members of the "C-C" branch exert their effects on the following cells: eosinophils which destroy parasites to lessen parasitic infection and cause chronic inflammation in the airways of the respiratory system; macrophages which suppress tumor formation in vertebrates; and basophils which release histamine which plays a role in allergic inflammation. However, members of one branch may exert an effect on cells which are normally responsive to the other branch of chemokines and, therefore, no precise role can be attached to the members of the branches.

While members of the C-C branch act predominantly on mononuclear cells and members of the C-X-C branch act predominantly on neutrophils a distinct chemoattractant property cannot be assigned to a chemokine based on this guideline. Some chemokines from one family show characteristics of the other.

The polypeptide of the present invention has the conserved cysteine residues of the "C-X-C" region, and has amino acid sequence homology to known chemokines.

Thus, there is a need for polypeptides that function as regulators of the migration of distinct cell types and of their roles in dysfunction and disease, since disturbances of such regulation may be involved in disorders relating to hemostasis, angiogenesis, tumor metastasis, cellular migration and ovulation, as well as neurogenesis. Therefore, there is a need for identification and characterization of such human polypeptides which can play a role in detecting, preventing, ameliorating or correcting such disorders.

SUMMARY OF THE INVENTION

The present invention provides isolated nucleic acid molecules comprising a polynucleotide encoding at least a portion of the CKα-5 polypeptide having the complete amino acid sequence shown in SEQ ID NO:2 or the complete amino acid sequence encoded by a cDNA clone deposited as plasmid DNA as ATCC® Deposit Number 209231 on Aug. 29, 1997. The ATCC® is located at 10801 University Boulevard, Manassas, Va. 20110-2209. The nucleotide sequence determined by sequencing the deposited CKα-5 clone, which is shown in FIG. 1 (SEQ ID NO:1), contains an open reading frame encoding a complete polypeptide of 254 amino acid residues, including an initiation codon encoding an N terminal methionine at nucleotide positions 542-544. Nucleic acid molecules of the invention include those encoding the complete amino acid sequence excepting the N-terminal methionine shown in SEQ ID NO:2, or the complete amino acid sequence excepting the N-terminal methionine encoded by a cDNA clone in ATCC® Deposit Number 209231, which molecules also can encode additional amino acids fused to the N-terminus of the CKα-5 amino acid sequence.

The polypeptide of the present invention has amino acid sequence homology to known chemokines, including the conserved C-X-C cysteine pattern characteristic of the alpha subfamily of chemokines beginning with the first cysteine from the amino terminus in SEQ ID NO:2.

CKα-5 also lacks the ELR motif found in some alpha chemokines immediately preceding the first cysteine residue, which is known to be required for the neutrophil and endothelial cell chemotactic activity as well as the angiogenic activity of IL-8.

The encoded polypeptide has a predicted leader sequence of 27 amino acids underlined in FIG. 1; and the amino acid sequence of the predicted mature CKα-5 protein is also shown in FIG. 1 as amino acid residues 28-254 and as residues 28-254 in SEQ ID NO:2. Further, the polypeptide is predicted to consist of an extracellular domain having the sequence from residues 28 to 205 in FIG. 1 (28 to 205 in SEQ ID NO:2), a transmembrane domain having a sequence from residue 206 to 227 in FIG. 1 (206 to 227 in SEQ ID NO:2), and an intracellular domain having a sequence from residue 228 to 254 in FIG. 1 (228 to 254 in SEQ ID NO:2).

Thus, one aspect of the invention provides an isolated polynucleotide comprising a nucleotide sequence selected from the group consisting of: (a) a nucleotide sequence encoding the CKα-5 polypeptide having the complete amino acid sequence in FIG. 1 (SEQ ID NO:2); (b) a nucleotide sequence encoding the CKα-5 polypeptide having the complete amino acid sequence in FIG. 1 (SEQ ID NO:2) excepting the N-terminal methionine (i.e., positions 2 to 254 of SEQ ID NO:2); (c) a nucleotide sequence encoding the predicted mature CKα-5 polypeptide having the amino acid sequence at positions 28-254 in FIG. 1 (28-254 in SEQ ID NO:2); (d) a nucleotide sequence encoding the predicted extracellular domain of the CKα-5 polypeptide having the amino acid sequence at positions 28-205 in FIG. 1 (28-205 in SEQ ID NO:2); (e) a nucleotide sequence encoding the CKα-5 polypeptide having the complete amino acid sequence encoded by the cDNA clone contained in ATCC® Deposit No. 209231; (f) a nucleotide sequence encoding the CKα-5 polypeptide having the complete amino acid sequence excepting the N terminal methionine encoded by the cDNA clone contained in ATCC® Deposit No. 209231; (g) a nucleotide sequence encoding the mature CKα-5 polypeptide encoded by the cDNA clone contained in ATCC® Deposit No. 209231; (h) a nucleotide sequence encoding the extracellular domain of CKα-5 encoded by the cDNA clone contained in ATCC® Deposit No. 209231; and (i) a nucleotide sequence complementary to any of the nucleotide sequences in (a), (b), (c), (d), (e), (f), (g) or (h) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f), (g), (h), or (i) above, or a polynucleotide which hybridizes under stringent hybridization conditions to a polynucleotide in (a), (b), (c), (d), (e), (f), (g), (h) or (i), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a CKα-5 polypeptide having an amino acid sequence in (a), (b), (c), (d), (e), (f), (g) or (h), above.

The present invention also relates to recombinant vectors, which include the isolated nucleic acid molecules of the present invention, and to host cells containing the recombinant vectors, as well as to methods of making such vectors and host cells and for using them for production of CKα-5 polypeptides or peptides by recombinant techniques.

The invention further provides an isolated CKα-5 polypeptide comprising an amino acid sequence selected from the group consisting of: (a) the amino acid sequence of the fill-length CKα-5 polypeptide having the complete amino acid sequence shown in SEQ ID NO:2 or the complete amino acid sequence encoded by the cDNA clone contained in the ATCC® Deposit No. 209231; (b) the amino acid sequence of the fill-length CKα-5 polypeptide having the complete amino acid sequence shown in SEQ ID NO:2 excepting the N-terminal methionine (i.e., positions 2 to 254 of SEQ ID NO:2) or the complete amino acid sequence excepting the N terminal methionine encoded by the cDNA clone contained in the ATCC® Deposit No. 209231; (c) the amino acid sequence of the mature CKα-5 polypeptide having the amino acid sequence shown in SEQ ID NO:2 as residues 28-254 or the amino acid sequence of the mature CKα-5 encoded by the cDNA clone contained in the ATCC® Deposit No. 209231; and (d) the amino acid sequence of the extracellular domain of the CKα-5 polypeptide having the amino acid sequence shown in SEQ ID NO:2 as residues 28-205 or the amino acid sequence of the extracellular domain of CKα-5 encoded by the cDNA clone contained in the ATCC® Deposit No. 209231. The polypeptides of the present invention also include polypeptides having an amino acid sequence at least 80% identical, more preferably at least 90% identical, and still more preferably 95%, 96%, 97%, 98% or 99% identical to those described in (a), (b), (c) or (d) above, as well as polypeptides having an amino acid sequence with at least 90% similarity, and more preferably at least 95% similarity, to those above. Polynucleotides encoding polypeptides having an amino acid sequence at least 80% identical, more preferably at least 90% identical, and still more preferably 95%, 96%, 97%, 98% or 99% identical to those described in (a), (b), (c) or (d) above, as well as polypeptides having an amino acid sequence with at least 90% similarity, and more preferably at least 95% similarity, to those above are also provided.

An additional embodiment of this aspect of the invention relates to a peptide or polypeptide which comprises the amino acid sequence of an epitope-bearing portion of a CKα-5 polypeptide having an amino acid sequence described in (a), (b), (c) or (d), above. Peptides or polypeptides having the amino acid sequence of an epitope-bearing portion of a CKα-5 polypeptide of the invention include portions of such polypeptides with at least six (6) or seven (7), preferably at least nine (9), and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a CKα-5 polypeptide having an amino acid sequence described in (a), (b), (c) or (d) above. The invention further provides methods for isolating antibodies that bind specifically to a CKα-5 polypeptide having an amino acid sequence as described herein. Such antibodies are useful diagnostically or therapeutically as described below.

The invention also provides for pharmaceutical compositions comprising CKα-5 polypeptides, particularly human CKα-5 polypeptides, which may be employed, for instance, to stimulate wound healing, to treat solid tumors, microbial infections, autoimmune diseases, liver cirrhosis, osteoarthritis and pulmonary fibrosis. Methods of treating individuals in need of CKα-5 polypeptides are also provided.

The invention further provides compositions comprising a CKα-5 polynucleotide or a CKα-5 polypeptide for administration to cells in vitro, to cells ex vivo and to cells in vivo, or to a multicellular organism. In certain particularly preferred embodiments of this aspect of the invention, the compositions comprise a CKα-5 polynucleotide for expression of a CKα-5 polypeptide in a host organism for treatment of disease. Particularly preferred in this regard is expression in a human patient for treatment of a dysfunction associated with aberrant endogenous activity of a CKα-5

The present invention also provides a screening method for identifying compounds capable of enhancing or inhibiting a biological activity of the CKα-5 polypeptide, which involves contacting a receptor which is enhanced by the CKα-5 polypeptide with the candidate compound in the presence of a CKα-5 polypeptide, assaying calcium mobilization or chemotactic activity of the cell expressing the receptor in the presence of the candidate compound and the CKα-5 polypeptide, and comparing the receptor activity to a standard level of activity, the standard being assayed when contact is made between the receptor and the CKα-5 polypeptide in the absence of the candidate compound. In this assay, an increase in calcium mobilization or chemotaxis over the standard indicates that the candidate compound is an agonist of CKα-5 activity and a decrease in calcium mobilization or chemotaxis compared to the standard indicates that the compound is an antagonist of CKα-5 activity.

It has been discovered that CKα-5 is expressed not only in neutrophils but also in monocytes, macrophages, liver, lung, testes, cerebellum and pineal gland. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the immune system, significantly higher or lower levels of CKα-5 gene expression may be detected in certain tissues (e.g., cancerous and wounded tissues) or bodily fluids (e.g., serum, plasma, urine, synovial fluid or spinal fluid) taken from an individual having such a disorder, relative to a "standard" CKα-5 gene expression level, i.e., the CKα-5 expression level in healthy tissue from an individual not having the immune system disorder. Thus, the invention provides a diagnostic method useful during diagnosis of such a disorder, which involves: (a) assaying CKα-5 gene expression level in cells or body fluid of an individual; (b) comparing the CKα-5 gene expression level with a standard CKα-5 gene expression level, whereby an increase or decrease in the assayed CKα-5 gene expression level compared to the standard expression level is indicative of disorder in the immune system.

An additional aspect of the invention is related to a method for treating an individual in need of an increased level of CKα-5 activity in the body comprising administering to such an individual a composition comprising a therapeutically effective amount of an isolated CKα-5 polypeptide of the invention or an agonist thereof.

A still further aspect of the invention is related to a method for treating an individual in need of a decreased level of CKα-5 activity in the body comprising, administering to such an individual a composition comprising a therapeutically effective amount of a CKα-5 antagonist. Preferred antagonists for use in the present invention are CKα-5-specific antibodies.

BRIEF DESCRIPTION OF THE FIGURES

FIG. 1A-C shows the nucleotide sequence (SEQ ID NO:1) and deduced amino acid sequence (SEQ ID NO:2) of CKα-5. The predicted leader sequence of about 27 amino acids is underlined. Note that the methionine residue at the beginning of the leader sequence in FIG. 1 is shown in position number (positive) 1, the leader positions in the corresponding sequence of SEQ ID NO:2 are designated with positive position numbers. Thus, the leader sequence positions 1 to 27 in FIG. 1 correspond to positions—1 to 27 in SEQ ID NO:2.

FIG. 2 shows the regions of identity between the amino acid sequence of the CKα-5 protein and translation product of the rat mRNA for MIP1-β (SEQ ID NO:3), as determined by Bestfit (Wisconsin Sequence Analysis Package, Version 8 for Unix, Genetics Computer Group, University Research Park, 575 Science Drive, Madison, Wis. 53711) using the default parameters.

DETAILED DESCRIPTION

Figure 3:
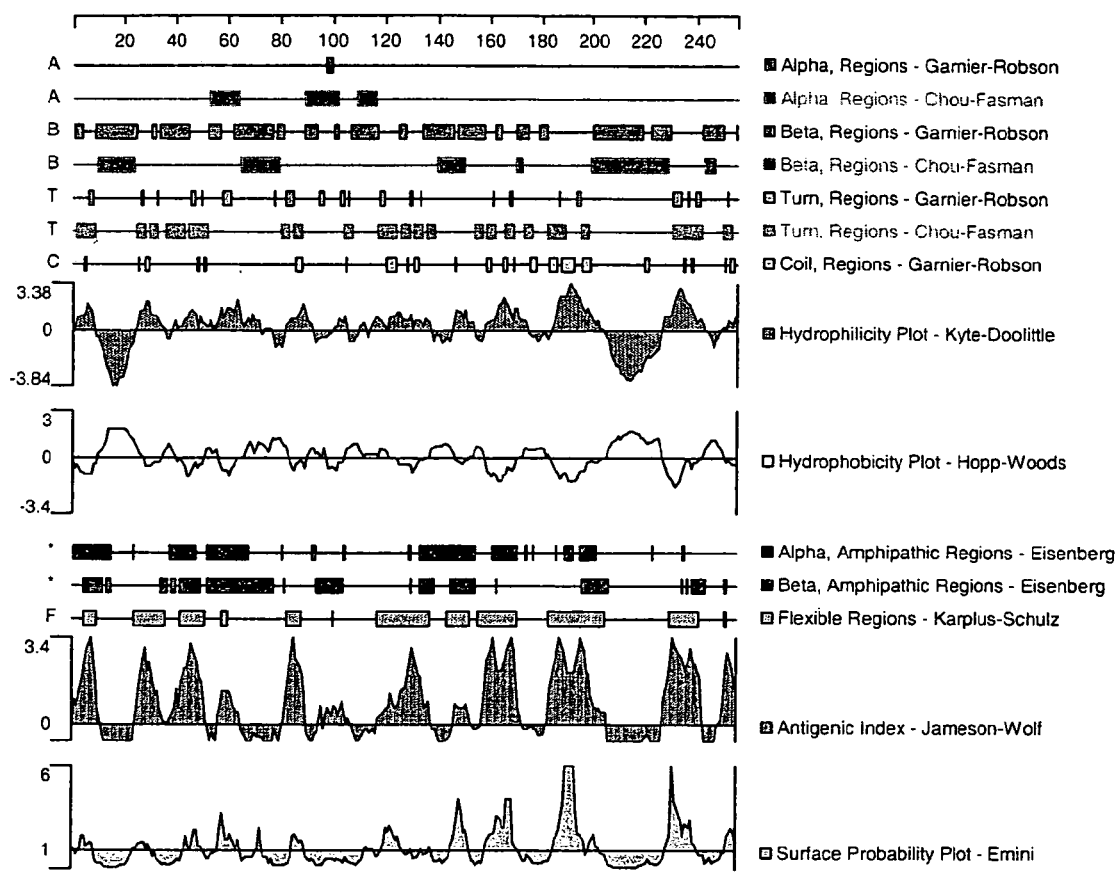
FIG. 3 shows an analysis of the CKα-5 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, the positive peaks indicate locations of the highly antigenic regions of the CKα-5 protein, i.e., regions from which epitope-bearing peptides of the invention can be obtained.

The present invention provides isolated nucleic acid molecules comprising a polynucleotide encoding a CKα-5 polypeptide having the amino acid sequence shown in SEQ ID NO:2, which was determined by sequencing cloned cDNAs. The nucleotide sequence shown in FIG. 1 (SEQ ID NO:1) was obtained by sequencing two cDNA clones: HMSCJ62 and HNFEM05. HMSCJ62 contains the full-length sequence shown in FIG. 1 and is deposited at Human Genome Sciences, Inc., 9410 Key West Ave., Rockville, Md. 20850. HNFEM05 contains all but the first 360 nucleotides (including all of the coding region) and was deposited as American Type Culture Collection ("ATCC®") Deposit No. 209231 on Aug. 29, 1997. The ATCC® is located at 10801 University Boulevard, Manassas, Va. 20110-2209.

The deposited clones are contained in the pBluescript SK(−) plasmid (Stratagene, La Jolla, Calif.).

The polypeptide of the present invention has amino acid sequence homology to known chemokines, including the conserved C-X-C cysteine pattern characteristic of the alpha subfamily of chemokines beginning with the first cysteine from the amino terminus in SEQ ID NO:2. The CKα-5 protein of the present invention also shares sequence homology with other chemokines including in particular the translation product of the human mRNA for MIP1-β (SEQ ID NO:3) as shown in FIG. 2.

Of the known members of the alpha chemokine family, the majority contain an ELR motif (e.g., IL-8, ENA-78, GCP2, GRO-α, PBP, CTAP-III and NAP-2) and others lack the ELR motif (IP-10, PF4 and MIG). CKα-5 lacks the ELR motif immediately preceding the first cysteine residue. It has been clearly shown that this ELR motif is required for the neutrophil and endothelial cell chemotactic activity as well as the angiogenic activity of L-8 (Strieter et al., *J. Biol. Chem.*, 270:27348-27357 (1995)). In addition, it has been shown that the ELR-C-X-C chemokines have in vitro and in vivo angiogenic activity, whereas the C-X-C chemokines lacking the ELR motif are actually angiostatic (Strieter et al., supra; Angiolillo et al., *J. Exp. Med.*, 182:155-162 (1995); and Koch et al., *Science*, 258:1798-1801 (1992)). In terms of a possible role of such factors in tumor angiogenesis, Smith et al., *J. Exp. Med.*, 179:1409-1415 (1994), has reported increased IL-8 levels in bronchogeneic carcinoma tumor tissues which appear to be produced from the tumor cells.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIG. 1 (SEQ ID NO:1), a nucleic acid molecule of the present invention encoding a CKα-5 polypeptide may be obtained using standard cloning and screening procedures, such as those for cloning cDNAs using mRNA as starting material. Illustrative of the invention, the nucleic acid molecule described in FIG. 1 (SEQ ID NO:1) was discovered in cDNA libraries derived primarily from immune-system tissues. Clone HMSCJ62 was isolated from a monocyte cDNA library and HNFEM05 was isolated from a neutrophil cDNA library.

Additional clones of the same gene were also identified in cDNA libraries from the following human tissues: colon and osteoclastoma.

The determined nucleotide sequence of the CKα-5 cDNA of FIG. 1 (SEQ ID NO:1) contains an open reading frame encoding a protein of 254 amino acid residues, with an initiation codon at nucleotide positions 542-544 of the nucleotide sequence in FIG. 1 (SEQ ID NO:1). The amino acid sequence of the CKα-5 protein shown in SEQ ID NO:2 is about 51% similar and 28% identical to the rat Macrophage Inflammatory Protein-1 β (FIG. 2), which can be accessed on GenBank as Accession No. gi|459148.

As one of ordinary skill would appreciate, due to the possibilities of sequencing errors discussed above, the actual complete CKα-5 polypeptide encoded by the deposited cDNA, which comprises about 254 amino acids, may be somewhat longer or shorter. More generally, the actual open reading frame may be anywhere in the range of ±20 amino acids, more likely in the range of ±10 amino acids, of that predicted from the methionine codon at the N-terminus shown in FIG. 1 (SEQ ID NO:1).

Leader and Mature Sequences

The amino acid sequence of the complete CKα-5 protein includes a leader sequence and a mature protein, as shown in SEQ ID NO:2. More in particular, the present invention provides nucleic acid molecules encoding a mature form of the CKα-5 protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature CKα-5 polypeptide having the amino acid sequence encoded by the cDNA clone identified as ATCC® Deposit No. 209231. By the "mature CKα-5 polypeptide having the amino acid sequence encoded by the cDNA clone in ATCC® Deposit No. 209231" is meant the mature form(s) of the CKα-5 protein produced by expression in a mammalian cell (e.g., COS cells, as described below) of the complete open reading frame encoded by the human DNA sequence of the clone contained in the deposited vector.

In addition, methods for predicting whether a protein has a secretory leader as well as the cleavage point for that leader sequence are available. For instance, the method of McGeoch (*Virus Res.* 3:271-286 (1985)) uses the information from a short N-terminal charged region and a subsequent uncharged region of the complete (uncleaved) protein. The method of von Heinje (*Nucleic Acids Res.* 14:4683-4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75-80% (von Heinje, supra). However, the two methods do not always produce the same predicted cleavage point(s) for a given protein.

In the present case, the deduced amino acid sequence of the complete CKα-5 polypeptide was analyzed by a computer program "PSORT", available from Dr. Kenta Nakai of the Institute for Chemical Research, Kyoto University (see K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated." The computation analysis above predicted one potential cleavage site within the complete amino acid sequence shown in SEQ ID NO:2; that is, between residues 27 and 28 in FIG. 1 and residues 27 and 28 in SEQ ID NO:2.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. By "isolated" the inventors intend to specifically exclude very large pieces of genetic material (200 kb+) such as isolated chromosomes and yeast artificial chromosomes (YACs).

Isolated nucleic acid molecules of the present invention include DNA molecules comprising an open reading frame (ORF) with an initiation codon at positions 542-544 of the nucleotide sequence shown in FIG. 1 (SEQ ID NO:1).

Also included are DNA molecules comprising the coding sequence for the predicted mature CKα-5 protein shown at positions 28-254 of SEQ ID NO:2.

In addition, isolated nucleic acid molecules of the invention include DNA molecules which comprise a sequence substantially different from those described above but which, due to the degeneracy of the genetic code, still encode a CKα-5 protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as $E.$ $coli$).

In another aspect, the invention provides isolated nucleic acid molecules encoding the CKα-5 polypeptide having an amino acid sequence encoded by the cDNA clone contained in the plasmid deposited as ATCC® Deposit No. 209231 on Aug. 29, 1997.

Preferably, this nucleic acid molecule will encode the mature polypeptide encoded by the above-described deposited cDNA clone.

The invention further provides an isolated nucleic acid molecule having the nucleotide sequence shown in FIG. 1 (SEQ ID NO: 1) or the nucleotide sequence of the CKα-5 cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the CKα-5 gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide comprising a nucleotide sequence representing the portion of SEQ ID NO:1 which consists of positions 1-1303, 542-1303, 622-1303, 625-1303, 628-1303, 631-1303, 634-1303, 637-1303, 640-1303, 643-1303, 646-1303, 649-1303, 652-1303, 652-787, 652-817, 652-847, 652-877, 652-907, 652-937, 652-967, 652-997, 652-1027, 652-1057, 652-1087, 652-1117, 652-1147, 652-1177, 652-1207, 652-1237, or 652-1267 of SEQ ID NO:1.

In addition, the following nucleic acid molecules having nucleotide sequences related to extensive portions of SEQ ID NO:1 have been identified: HNFCO09R (SEQ ID NO:4) from clone HNFCO09; HNEDS26R (SEQ ID NO:5) from clone HNEDS26R; HOABD47R (SEQ ID NO:6) from clone HOABD47; HTEIR41R (SEQ ID NO:7) from clone HTEIR41; HMNAD36R (SEQ ID NO:8) from clone HMNAD36; and HTEDQ07RA (SEQ ID NO:20) from clone HTEDQ07.

The following publicly available expressed sequence tags ("ESTs"), which relate to portions of SEQ ID NO: 1, have also been identified: GenBank Accession No. AA130776 (SEQ ID NO:9); GenBank Accession No. AA290712 (SEQ ID NO:10); GenBank Accession No. AA366329 (SEQ ID NO:11); GenBank Accession No. AA121716 (SEQ ID NO:12); GenBank Accession No. AA146672 (SEQ ID NO:13); GenBank Accession No. AA149359 (SEQ ID NO:14); GenBank Accession No. AA569970 (SEQ ID NO:21); and GenBank Accession No. AA994552 (SEQ ID NO:22).

Polynucleotides of the invention preferably are not, and do not comprise, one or more of the forgoing sequences 1-14 and 20-22.

Further, the invention includes a polynucleotide comprising any portion of at least about 17 nucleotides, preferably at least about 20, 25, or 30, and most preferably at least about 50 nucleotides, of SEQ ID NO:1 from nucleotide 542 to 1303.

The invention also includes a polynucleotide comprising any portion of at least about 500, preferably about 600 nucleotides, of SEQ ID NO:1, preferably from residue 542 to 1,303. Particularly preferred nucleotide fragments in this regard include the fragment from nucleotide 622 to 1,303 in SEQ ID NO:1.

More generally, by a fragment of an isolated nucleic acid molecule having the nucleotide sequence of the deposited cDNA or the nucleotide sequence shown in FIG. 1 (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-1,000 nt in length are also useful according to the present invention as are fragments corresponding to most, if not all, of the nucleotide sequence of the deposited cDNA or as shown in FIG. 1 (SEQ ID NO:1). By a fragment at least 20 nt in length, for example, is intended fragments which include 20 or more contiguous bases from the nucleotide sequence of the deposited cDNA or the nucleotide sequence as shown in FIG. 1 (SEQ ID NO:1). Preferred nucleic acid fragments of the present invention include nucleic acid molecules encoding epitope-bearing portions of the CKα-5 polypeptide as identified from the Jameson-Wolf antigenic index shown in FIG. 3 and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC® Deposit No. 209231. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 (SEQ ID NO:1)). Of course, a polynucleotide which hybridizes only to a poly A sequence (such as the 3' terminal poly(A) tract of the CKα-5 cDNA shown in FIG. 1 (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a CKα-5 polypeptide may include, but are not limited to those encoding the amino acid sequence of the mature polypeptide, by itself; and the coding sequence for the mature polypeptide and additional sequences, such as those encoding the about 27 amino acid leader or secretory sequence, such as a pre-, or pro- or prepro- protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including siplicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the CKα-5 fused to Fc at the N- or C-terminus.

Variant and Mutant Polynucleotides

The present invention further relates to variants of the nucleic acid molecules of the present invention, which encode portions, analogs or derivatives of the CKα-5 protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the CKα-5 protein or portions thereof. Also especially preferred in this regard are conservative substitutions.

Most highly preferred are nucleic acid molecules encoding the mature protein having the amino acid sequence shown in SEQ ID NO:2 or the mature CKα-5 amino acid sequence encoded by the deposited cDNA clone either of which may be modified so as to encode an amino terminal methionine or other N- or C-terminal fusion peptides or polypeptides.

Further embodiments include an isolated polynucleotide comprising a nucleotide sequence at least 90% identical, and more preferably at least 95%, 96%, 97%, 98% or 99% identical to a nucleic acid sequence selected from the group consisting of: (a) a nucleotide sequence encoding the CKα-5 polypeptide shown as SEQ ID NO:2; (b) a nucleotide sequence encoding the CKα-5 polypeptide shown as residues 1-254 of SEQ ID NO:2; (c) a nucleotide sequence encoding the predicted mature CKα-5 shown as residues 28-254 in SEQ ID NO:2; (d) a nucleotide sequence encoding the predicted extracellular domain of the CKα-5 polypeptide shown as residues 28-205 in SEQ ID NO:2; (e) a nucleotide sequence encoding the CKα-5 polypeptide having the complete amino acid sequence encoded by the cDNA clone contained in ATCC® Deposit No. 209231; (f) a nucleotide sequence encoding the CKα-5 polypeptide having the complete amino acid sequence excepting the N terminal methionine encoded by the cDNA clone contained in ATCC® Deposit No. 209231; (g) a nucleotide sequence encoding the mature CKα-5 polypeptide having the amino acid sequence encoded by the cDNA clone contained in ATCC® Deposit No. 209231; (h) a nucleotide sequence encoding the extracellular domain of the CKα-5 polypeptide having the amino acid sequence encoded by the cDNA clone contained in ATCC® Deposit No. 209231; and (i) a nucleotide sequence complementary to any of the nucleotide sequences in (a), (b), (c), (d), (e), (f), (g) or (h) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f), (g), (h) or (i) above, or a polynucleotide which hybridizes under stringent hybridization conditions to a polynucleotide in (a), (b), (c), (d), (e), (f), (g), (h) or (i), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a CKα-5 polypeptide having an amino acid sequence in (a), (b), (c), (d), (e), (f), (g) or (h) above.

The present invention also relates to recombinant vectors, which include the isolated nucleic acid molecules of the present invention, and to host cells containing the recombinant vectors, as well as to methods of making such vectors and host cells and for using them for production of CKα-5 polypeptides or peptides by recombinant techniques.

By a polynucleotide having a nucleotide sequence at least, for example, 95% "identical" to a reference nucleotide sequence encoding a CKα-5 polypeptide is intended that the nucleotide sequence of the polynucleotide is identical to the reference sequence except that the polynucleotide sequence may include up to five point mutations per each 100 nucleotides of the reference nucleotide sequence encoding the CKα-5 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 (SEQ ID NO:1) or to the nucleic acid sequence of the deposited cDNA, irrespective of whether they encode a polypeptide having CKα-5 activity. This is because even where a particular nucleic acid molecule does not encode a polypeptide having CKα-5 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having CKα-5 activity include, inter alia, (1) isolating the CKα-5 gene or allelic variants thereof in a cDNA library; (2) in situ hybridization (e.g., "FISH") to metaphase chromosomal spreads to provide precise chromosomal location of the CKα-5 gene, as described in Verma et al., Human Chromosomes: A Manual of Basic Techniques, Pergamon Press, New York (1988); and Northern Blot analysis for detecting CKα-5 mRNA expression in specific tissues.

Preferred, however, are nucleic acid molecules having sequences at least 90%, 95%, 96%, 97%, 98% or 99% identical to the nucleic acid sequence shown in FIG. 1 (SEQ ID NO:1) or to the nucleic acid sequence of the deposited cDNA which do, in fact, encode a polypeptide having CKα-5 protein activity. By "a polypeptide having CKα-5 activity" is intended polypeptides exhibiting activity similar, but not necessarily identical, to an activity of the extracellular portion of the complete CKα-5 protein. One such activity believed to be possessed by such polypeptides is the ability to modulate colony formation of bone marrow progenitor cells, as does Human Chemokine HCC-1. An in vitro colony forming assay for measuring the extent of inhibition of myeloid progenitor cells is described in Young et al., *The Journal of Immunology* 155:2661-2667 (1995). Briefly, the assay involves collecting human or mouse bone marrow cells and plating the same on agar, adding one or more growth factors and either (1) transfected host cell-supernatant containing CKα-5 protein (or a candidate polypeptide) or (2) nontransfected host cell-supernatant control, and measuring the effect on colony formation by murine and human CFU-granulocyte-macrophages (CFU-GM), by human burst-forming unit-erythroid (BFU-E), or by human CFU granulocyte-erythroid-macrophage-megakaryocyte (CFU-GEMM). Such activity is useful for protecting myeloid progenitor cells during chemotherapy.

CKα-5 protein modulates immune system cell proliferation and differentiation in a dose-dependent manner in the above-described assay. Thus, "a polypeptide having CKα-5 protein activity" includes polypeptides that also exhibit any of the same myeloid progenitor modulation activities in the above-described assays in a dose-dependent manner. Although the degree of dose-dependent activity need not be identical to that of the CKα-5 protein, preferably, "a polypeptide having CKα-5 protein activity" will exhibit substantially similar dose-dependence in a given activity as compared to the CKα-5 protein (i.e., the candidate polypeptide will exhibit greater activity or not more than about 25-fold less and, preferably, not more than about tenfold less activity relative to the reference CKα-5 protein).

Like other CXC chemokines, CKα-5 exhibits activity on leukocytes including for example monocytes, lymphocytes and neutrophils. For this reason CKα-5 is active in directing the proliferation, differentiation and migration of these cell types. Such activity is useful for immune enhancement or suppression, myeloprotection, stem cell mobilization, acute and chronic inflammatory control and treatment of leukemia. Assays for measuring such activity are known in the art. For example, see Peters et al., *Immun. Today* 17:273 (1996); Young et al., *J. Exp. Med.* 182:1111 (1995); Caux et al., *Nature* 390:258 (1992); and Santiago-Schwarz et al., *Adv. Exp. Med. Biol.* 378:7 (1995)." The assays and protocols from each of the forgoing journal articles are incorporated herein by reference.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having CKα-5 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having CKα-5 protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of CKα-5 polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., J. Molecular Recognition 8:52-58 (1995) and K. Johanson et al., J. Biol. Chem. 270:9459-9471 (1995).

The CKα-5 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides an isolated CKα-5 polypeptide having the amino acid sequence encoded by the deposited cDNA, or the amino acid sequence in SEQ ID NO:2, or a peptide or polypeptide comprising a portion of the above polypeptides.

Variant and Mutant Polypeptides

To improve or alter the characteristics of CKα-5 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.,* 268:2984-2988 (1993) reported modified KGF proteins that had heparin binding activity even if 3, 8, or 27 amino-terminal amino acid residues were missing. In the present case, since the protein of the invention is a member of the chemokine polypeptide family, deletions of N-terminal amino acids up to the first "Cys" required for formation of a disulfide bridge may retain some biological activity such as receptor binding or modulation of target cell activities. Polypeptides having further N-terminal deletions including the cysteine residue at position 38 in FIG. 1 (position 11 in SEQ ID NO:2) would not be expected to retain such biological activities because it is known that this residue in a chemokine-related polypeptide is required for forming a disulfide bridge to provide structural stability which is needed for receptor binding and signal transduction.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the CKα-5 protein shown in SEQ ID NO:2, up to the cysteine residue at position number 38, and polynucleotides encoding such polypeptides. In particular, the present invention provides polypeptides comprising the amino acid sequence of residues n-205 of SEQ ID NO:2, where n is an integer in the range of 24-38, and Cys-38 is the position of the first residue from the N-terminus of the extracellular domain of the CKα-5 polypeptide (shown in SEQ ID NO:2) believed to be required for receptor binding activity of the CKα-5 protein.

More in particular, the invention provides polypeptides comprising an amino acid sequence selected from the group consisting of: 24 to 205, 25 to 205, 26 to 205, 27 to 205, 28 to 205, 29 to 205, 30 to 205, 31 to 205, 32 to 205, 33 to 205, 34 to 205, 35 to 205, 36 to 205, 37 to 205, and 38 to 205, all of SEQ ID NO:2. Polynucleotides encoding such polypeptides are also provided.

Similarly, many examples of biologically functional C-terminal deletion muteins are known. For instance, Interferon gamma shows up to ten times higher activities by deleting 8-10 amino acid residues from the carboxy terminus of the protein (Döbeli et al., *J. Biotechnology* 7:199-216 (1988). In the present case, since the protein of the invention is a member of the chemokine polypeptide family, deletions of C-terminal amino acids up to the cysteine at position 82 of SEQ ID NO:2 may retain some biological activity such as receptor binding or modulation of target cell activities. Polypeptides having further C-terminal deletions including the cysteine residue at position 82 of FIG. 1 (82 of SEQ ID NO:2) would not be expected to retain such biological activities because it is known that this residue in a chemokine-related polypeptide is required for forming a disulfide bridge to provide structural stability which is needed for receptor binding and signal transduction.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the CKα-5 shown in SEQ ID NO:2, up to the cysteine residue at position 82 of SEQ ID NO:2, and polynucleotides encoding such polypeptides. In particular, the present invention provides polypeptides having the amino acid sequence of residues (24)-m of the amino acid sequence in SEQ ID NO:2, where m is any integer in the range of 82 to 205, and residue cysteine-82 is the position of the first residue from the C-terminus of the complete CKα-5 polypeptide (shown in SEQ ID NO:2) believed to be required for receptor binding and target cell modulation activities of the CKα-5 protein.

More in particular, the invention provides polypeptides comprising an amino acid sequence selected from the group consisting of: 24 to 82, 24 to 83, 24 to 84, 24 to 85, 24 to 86, 24 to 87, 24 to 88, 24 to 89, 24 to 90, 24 to 91, 24 to 92, 24 to 93, 24 to 94, 24 to 95, 24 to 96, 24 to 97, 24 to 98, 24 to 99, 24 to 100, 24 to 101, 24 to 102, 24 to 103, 24 to 104, 24 to 105, 24 to 106, 24 to 107, 24 to 108, 24 to 109, 24 to 110, 24 to 111, 24 to 112, 24 to 113, 24 to 114, 24 to 115, 24 to 116, 24 to 117, 24 to 118, 24 to 119, 24 to 120, 24 to 121, 24 to 122, 24 to 123, 24 to 124, 24 to 125, 24 to 126, 24 to 127, 24 to 128, 24 to 129, 24 to 130, 24 to 131, 24 to 132, 24 to 133, 24 to 134, 24 to 135, 24 to 136, 24 to 137, 24 to 138, 24 to 139, 24 to 140, 24 to 141, 24 to 142, 24 to 143, 24 to 144, 24 to 145, 24 to 146, 24 to 147, 24 to 148, 24 to 149, 24 to 150, 24 to 151, 24 to 152, 24 to 153, 24 to 154, 24 to 155, 24 to 156, 24 to 157, 24 to 158, 24 to 159, 24 to 160, 24 to 161, 24 to 162, 24 to 163, 24 to 164, 24 to 165, 24 to 166, 24 to 167, 24 to 168, 24 to 169, 24 to 170, 24 to 171, 24 to 172, 24 to 173, 24 to 174, 24 to 175, 24 to 176, 24 to 177, 24 to 178, 24 to 179, 24 to 180, 24 to 181, 24 to 182, 24 to 183, 24 to 184, 24 to 185, 24 to 186, 24 to 187, 24 to 188, 24 to 189, 24 to 190, 24 to 191, 24 to 192, 24 to 193, 24 to 194, 24 to 195, 24 to 196, 24 to 196, 24 to 197, 24 to 198, 24 to 199, 24 to 200, 24 to 201, 24 to 202, 24 to 203, 24 to 204, and 24 to 205, all of SEQ ID NO:2. Polynucleotides encoding these polypeptides also are provided.

The invention also provides polypeptides having one or more amino acids deleted from both the amino and the carboxyl termini of the soluble form (extracellular domain), which may be described generally as having residues n-m of SEQ ID NO:2, where n and m are integers as described above. Particularly preferred are polypeptides comprising an amino acid sequence selected from the group consisting of: 38 to 82, 38 to 83, 37 to 84, 37 to 85, 37 to 86, 37 to 87, 37 to 88, 37 to 89, 36 to 90, 36 to 91, 36 to 92, 36 to 93, 36 to 94, 36 to 95, 36 to 96, 36 to 97, 36 to 98, 36 to 99, 36 to 100, 35 to 101, 35 to 102, 35 to 103, 35 to 104, 35 to 105, 35 to 106, 35 to 107, 35 to 108, 35 to 109, 35 to 110, 35 to 111, 34 to 112, 34 to 113, 34 to 114, 34 to 115, 34 to 116, 34 to 117, 34 to 118, 34 to 119, 34 to 120, 34 to 121, 34 to 122, 34 to 123, 34 to 124, 34 to 125, 34 to 126, 34 to 127, 33 to 128, 33 to 129, 33 to 130, 33 to 131, 33 to 132, 33 to 133, 33 to 134, 33 to 135, 33 to 136, 33 to 137, 33 to 138, 33 to 139, 33 to 140, 33 to 141, 33 to 142, 33 to 143, 33 to 144, 33 to 145, 33 to 146, 33 to 147, 33 to 148, 33 to 149, 33 to 150, 33 to 151, 33 to 152, 33 to 153, 33 to 154, 33 to 155, 33 to 156, 33 to 157, 33 to 158, 33 to 159, 33 to 160, 33 to 161, 33 to 162, 33 to 163, 33 to 164, 33 to 165, 33 to 166, 33 to 167, 33 to 168, 33 to 169, 33 to 170, 33 to 171, 33 to 172, 33 to 173, 33 to 174, 33 to 175, 33 to 176, 33 to 177, 33 to 178, 33 to 179, 33 to 180, 33 to 181, 33 to 182, 33 to 183, 33 to 184, 32 to 185, 32 to 186, 32 to 187, 32 to 188, 32 to 189, 32 to 190, 32 to 191, 32 to 192, 32 to 193, 32 to 194, 32 to 195, 32 to 196, 31 to 197, 31 to 198, 31 to 199, 31 to 200, 31 to 201, 31 to 202, 31 to 203, 31 to 204, and 31 to 205, all of SEQ ID NO:2. Polynucleotides encoding these polypeptides also are provided.

Also included are a nucleotide sequence encoding a polypeptide consisting of a portion of the complete CKα-5 amino acid sequence encoded by the cDNA clone contained in ATCC® Deposit No. 209231, where this portion excludes from 23 to about 37 amino acids from the amino terminus of the extracellular domain of the CKα-5 polypeptide encoded by the cDNA clone contained in ATCC® Deposit No. 209231, or from 49 to about 172 amino acids from the carboxy terminus, or any combination of the above amino terminal and carboxy terminal deletions, of the extracellular domain encoded by the cDNA clone contained in ATCC® Deposit No. 209231. Polynucleotides encoding all of the above deletion mutant polypeptide forms also are provided.

Other Mutants

In addition to terminal deletion forms of the protein discussed above, it also will be recognized by one of ordinary skill in the art that some amino acid sequences of the CKα-5 polypeptide can be varied without significant effect of the structure or function of the protein. If such differences in sequence are contemplated, it should be remembered that there will be critical areas on the protein which determine activity.

Thus, the invention further includes variations of the CKα-5 polypeptide which show substantial CKα-5 polypeptide activity or which include regions of CKα-5 protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. Typically seen as conservative substitutions are those shown in Table 1.

Thus, the fragment, derivative or analog of the polypeptide of SEQ ID NO:2, or that encoded by the deposited cDNA, may be (i) one in which one or more of the amino acid residues are substituted with a conserved or nonconserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein Thus, the CKα-5 of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the CKα-5 protein of the present invention that are essential for function can be identified by methods known in the art, such as site-directed mutagenesis or alanine-scanning mutagenesis (Cunningham and Wells, Science 244:1081-1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331-340 (1967); Robbins et al., Diabetes 36: 838-845 (1987); Cleland et al., *Crit. Rev. Therapeutic Drug Carrier Systems* 10:307-377 (1993).

Replacement of amino acids can also change the selectivity of the binding of a ligand to cell surface receptors. For example, Ostade et al., *Nature* 361:266-268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

As described above CKα-5 lacks an ELR motif. By making a specific mutation in CKα-5 to include an ELR motif in the position where such a motif is typically found in related chemokines, CKα-5 will act as an antagonist, thus possessing angiogenic activity. Accordingly, polypeptides of the present invention include CKα-5-ELR mutants. Such CKα-5-ELR mutants are comprised of the full-length or preferably the mature CKα-5 protein. Further, since CKα-5 is a member of the chemokine-related protein family, to modulate rather than completely eliminate biological activities of CKα-5 preferably mutations are made in sequences encoding amino acids in the CKα-5 extracellular domain, i.e., in positions 28 to 205 of SEQ ID NO:2, more preferably in residues within this region which are not conserved in all members of the chemokine family. As is known in the art, the four spatially conserved cysteines present in all chemokines, positions 38, 40, 68 and 82 in CKα-5, are required for the formation of two disulfide bridges. Thus, it is preferable not to alter any of the four cysteine residues located at positions 38, 40, 68 and 82 in SEQ ID NO:2. Also forming part of the present invention are isolated polynucleotides comprising nucleic acid sequences which encode the above CKα-5 mutants.

The polypeptides of the present invention are preferably provided in an isolated form, and preferably are substantially purified. A recombinantly produced version of the CKα-5 polypeptide can be substantially purified by the one-step method described in Smith and Johnson, *Gene* 67:31-40 (1988). Polypeptides of the invention also can be purified from natural or recombinant sources using anti-CKα-5 antibodies of the invention in methods which are well known in the art of protein purification.

The invention further provides an isolated CKα-5 polypeptide comprising an amino acid sequence selected from the group consisting of: (a) the amino acid sequence of the full-length CKα-5 polypeptide having the complete amino acid sequence shown in SEQ ID NO:2 or the complete amino acid sequence encoded by the cDNA clone contained in the ATCC® Deposit No. 209231; (b) the amino acid sequence of the full-length CKα-5 polypeptide having the complete amino acid sequence shown in SEQ ID NO:2 excepting the N-terminal methionine (i.e., positions 2 to 254 of SEQ ID NO:2) or the complete amino acid sequence excepting the N terminal methionine encoded by the cDNA clone contained in the ATCC® Deposit No. 209231; (c) the amino acid sequence of the mature CKα-5 polypeptide having the amino acid sequence shown in SEQ ID NO:2 as residues 28-254 or the amino acid sequence of the mature CKα-5 encoded by the cDNA clone contained in the ATCC® Deposit No. 209231; and (d) the amino acid sequence of the extracellular domain of the CKα-5 polypeptide having the amino acid sequence shown in SEQ ID NO:2 as residues 28-205 or the amino acid sequence of the extracellular domain of the CKα-5 polypeptide encoded by the cDNA clone contained in the ATCC® Deposit No. 209231.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids. Polynucleotides encoding such variant polypeptides are also provided.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482-489, 1981) to find the best segment of similarity between two sequences.

By a polypeptide having an amino acid sequence at least, for example, 95% "identical" to a reference amino acid sequence of a CKα-5 polypeptide is intended that the amino acid sequence of the polypeptide is identical to the reference sequence except that the polypeptide sequence may include up to five amino acid alterations per each 100 amino acids of the reference amino acid of the CKα-5 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting CKα-5 protein expression as described below or as agonists and antagonists capable of enhancing or inhibiting CKα-5 protein function. Further, such polypeptides can be used in the yeast two-hybrid system to "capture" CKα-5 protein binding proteins which are also candidate agonists and antagonists according to the present invention. The yeast two hybrid system is described in Fields and Song, Nature 340:245-246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," Science, 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., Cell 37:767-778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate CKα-5-specific antibodies include: a polypeptide comprising amino acid residues from about Tyr-39 to about Ser-51 in SEQ ID NO:2; a polypeptide comprising amino acid residues from about Cys-82 to about Val-90 in SEQ ID NO:2; a polypeptide comprising amino acid residues from about Thr-91 to about Pro-110 in SEQ ID NO:2; a polypeptide comprising amino acid residues from about Ser-120 to about Ile-145; a polypeptide comprising amino acid residues from about Asp-4 to about Ser-9; a polypeptide comprising amino acid residues from about Lys-42 to about Pro-50; a polypeptide comprising amino acid residues from about Gly-83 to about Pro-88; a polypeptide comprising amino acid residues from about Glu-128 to about Asp-133; a polypeptide comprising amino acid residues from about Ser-159 to about Thr-170; a polypeptide comprising amino acid residues from about Glu-184 to about Pro-198; a polypeptide comprising amino acid residues from about Lys-228 to about Asp-240; and a polypeptide comprising amino acid residues from about Pro-250 to about Asn-253. These polypeptide fragments have been determined to bear antigenic epitopes of the CKα-5 protein by the analysis of the Jameson-Wolf antigenic index, as shown in FIG. 3, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." Proc. Natl. Acad. Sci. USA 82:5131-5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910-914; and Bittle, F. J. et al., J. Gen. Virol. 66:2547-2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, CKα-5 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84-86 (1988)). Fusion proteins that have a disulfide-linked dimeric structure due to the IgG part can also be more efficient in binding and neutralizing other molecules than the monomeric CKα-5 protein or protein fragment alone (Fountoulakis et al., *J. Biochem.* 270:3958-3964 (1995)).

Antibodies

CKα-5-protein specific antibodies for use in the present invention can be raised against the intact CKα-5 protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to CKα-5 protein. Fab and F(ab')2 fragments lack the Fc fragment of intact antibody, clear more rapidly from the circulation, and may have less non-specific tissue binding of an intact antibody (Wahl et al., *J Nucl. Med.* 24:316-325 (1983)). Thus, these fragments are preferred.

The antibodies of the present invention may be prepared by any of a variety of methods. For example, cells expressing the CKα-5 protein or an antigenic fragment thereof can be administered to an animal in order to induce the production of sera containing polyclonal antibodies. In a preferred method, a preparation of CKα-5 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or CKα-5 protein binding fragments thereof). Such monoclonal antibodies can be prepared using hybridoma technology (Köhler et al., *Nature* 256:495 (1975); Köhler et al., *Eur. J. Immunol.* 6:511 (1976); Köhler et al., *Eur. J. Immunol.* 6:292 (1976); Hammerling et al., in: *Monoclonal Antibodies and T-Cell Hybridomas*, Elsevier, N.Y., (1981) pp. 563-681). In general, such procedures involve immunizing an animal (preferably a mouse) with a CKα-5 protein antigen or, more preferably, with a CKα-5 protein-expressing cell. Suitable cells can be recognized by their capacity to bind anti-CKα-5 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the CKα-5 protein antigen.

Alternatively, additional antibodies capable of binding to the CKα-5 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, CKα-5-protein specific antibodies are used to immunize an animal, preferably a mouse. The splenocytes of such an animal are then used to produce hybridoma cells, and the hybridoma cells are screened to identify clones which produce an antibody whose ability to bind to the CKα-5 protein-specific antibody can be blocked by the CKα-5 protein antigen. Such antibodies comprise anti-idiotypic antibodies to the CKα-5 protein-specific antibody and can be used to immunize an animal to induce formation of further CKα-5 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, CKα-5 protein-binding fragments can be produced through the application of recombinant DNA technology or through synthetic chemistry.

For in vivo use of anti-CKα-5 in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Immune System-Related Disorders

Diagnosis

The present inventors have discovered that CKα-5 is expressed in neutrophils and monocytes. For a number of immune system-related disorders, substantially altered (increased or decreased) levels of CKα-5 gene expression can be detected in immune system tissue or other cells or bodily fluids (e.g., sera, plasma, urine, synovial fluid or spinal fluid) taken from an individual having such a disorder, relative to a "standard" CKα-5 gene expression level, that is, the CKα-5 expression level in immune system tissues or bodily fluids from an individual not having the immune system disorder. Thus, the invention provides a diagnostic method useful during diagnosis of an immune system disorder, which involves measuring the expression level of the gene encoding the CKα-5 protein in immune system tissue or other cells or body fluid from an individual and comparing the measured gene expression level with a standard CKα-5 gene expression level, whereby an increase or decrease in the gene expression level compared to the standard is indicative of an immune system disorder.

In particular, it is believed that certain tissues in mammals with cancer, particularly osteosarcoma, express significantly altered levels of the CKα-5 protein and mRNA encoding the CKα-5 protein when compared to a corresponding "standard" level. Further, it is believed that altered levels of the CKα-5 protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of an immune system disorder, including cancers of the skeletal and immune systems, which involves measuring the expression level of the gene encoding the CKα-5 protein in immune or skeletal system tissue or other cells or body fluid from an individual and comparing the measured gene expression level with a standard CKα-5 gene expression level, whereby an increase or decrease in the gene expression level compared to the standard is indicative of an immune system disorder.

Where a diagnosis of a disorder in the immune system, including diagnosis of a tumor, has already been made according to conventional methods, the present invention is useful as a prognostic indicator, whereby patients exhibiting enhanced or depressed CKα-5 gene expression will experience a worse clinical outcome relative to patients expressing the gene at a level nearer the standard level.

By "assaying the expression level of the gene encoding the CKα-5 protein" is intended qualitatively or quantitatively measuring or estimating the level of the CKα-5 protein or the level of the mRNA encoding the CKα-5 protein in a first biological sample either directly (e.g., by determining or estimating absolute protein level or mRNA level) or relatively (e.g., by comparing to the CKα-5 protein level or mRNA level in a second biological sample). Preferably, the CKα-5 protein level or mRNA level in the first biological sample is measured or estimated and compared to a standard CKα-5 protein level or mRNA level, the standard being taken from a second biological sample obtained from an individual not having the disorder or being determined by averaging levels from a population of individuals not having a disorder of the immune system. As will be appreciated in the art, once a standard CKα-5 protein level or mRNA level is known, it can be used repeatedly as a standard for comparison.

By "biological sample" is intended any biological sample obtained from an individual, body fluid, cell line, tissue culture, or other source which contains CKα-5 protein or mRNA. As indicated, biological samples include body fluids (such as sera, plasma, urine, synovial fluid and spinal fluid) which contain free CKα-5 protein, immune and skeletal system tissue, and other tissue sources found to express complete mature CKα-5 or a CKα-5 receptor. Methods for obtaining tissue biopsies and body fluids from mammals are well known in the art. Where the biological sample is to include mRNA, a tissue biopsy is the preferred source.

The present invention is useful for diagnosis or treatment of various immune system-related disorders in mammals, preferably humans. Such disorders include tumors, cancers, sarcomas such as osteosarcoma, interstitial lung disease (such as Langerhans cell granulomatosis) and any disregulation of immune cell function including, but not limited to, autoimmunity, arthritis, leukemias, lymphomas, immunosuppression, immunity, humoral immunity, inflammatory bowel disease, myelo suppression, and the like.

Total cellular RNA can be isolated from a biological sample using any suitable technique such as the single-step guanidinium-thiocyanate-phenol-chloroform method described in Chomczynski and Sacchi, *Anal. Biochem.* 162: 156-159 (1987). Levels of mRNA encoding the CKα-5 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying CKα-5 protein levels in a biological sample can occur using antibody-based techniques. For example, CKα-5 protein expression in tissues can be studied with classical immunohistological methods (Jalkanen, M., et al., *J. Cell. Biol.* 101:976-985 (1985); Jalkanen, M., et al., *J. Cell. Biol.* 105:3087-3096 (1987)). Other antibody-based methods useful for detecting CKα-5 protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying CKα-5 protein levels in a biological sample obtained from an individual, CKα-5 protein can also be detected in vivo by imaging. Antibody labels or markers for in vivo imaging of CKα-5 protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A CKα-5 protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain CKα-5 protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

As noted above, CKα-5 polynucleotides and polypeptides are useful for diagnosis of conditions involving abnormally high or low expression of CKα-5 activities. Given the cells and tissues where CKα-5 is expressed as well as the activities modulated by CKα-5, it is readily apparent that a substantially altered (increased or decreased) level of expression of CKα-5 in an individual compared to the standard or "normal" level produces pathological conditions related to the bodily system(s) in which CKα-5 is expressed and/or is active.

It will also be appreciated by one of ordinary skill that, since the CKα-5 protein of the invention is a member of the chemokine family the mature secreted form of the protein may be released in soluble form from the cells which express the CKα-5 by proteolytic cleavage. Therefore, when CKα-5 is added from an exogenous source to cells, tissues or the body of an individual, the protein will exert its physiological activities on its target cells of that individual. Also, cells expressing this transmembrane protein may be added to cells, tissues or the body of an individual and these added cells will bind to cells expressing receptor for CKα-5, whereby the cells expressing CKα-5 can cause actions, e.g., cell stimulation, on the receptor-bearing target cells.

Therefore, it will be appreciated that conditions caused by a decrease in the standard or normal level of CKα-5 activity in an individual, particularly disorders of the immune system, can be treated by administration of CKα-5 polypeptide in the form of the soluble extracellular domain or cells expressing the complete protein. Thus, the invention also provides a method of treatment of an individual in need of an increased level of CKα-5 activity comprising administering to such an individual a pharmaceutical composition comprising an amount of an isolated CKα-5 polypeptide of the invention, effective to increase the CKα-5 activity level in such an individual.

Since CKα-5 lacks an ELR motif, it also should be an angiostatic factor rather than an angiogenic factor. In addition, since CKα-5 inhibits endothelial cell function, it will have a wide range of anti-inflammatory activities. CKα-5 may be employed as an anti-neovascularizing agent to treat solid tumors by stimulating the invasion and activation of host defense cells, e.g., cytotoxic T cells and macrophages and by inhibiting the angiogenesis of tumors. Those of skill in the art will recognize other non-cancer indications where blood vessel proliferation is not wanted. They may also be employed to enhance host defenses against resistant chronic and acute infections, for example, myobacterial infections via the attraction and activation of microbicidal leukocytes. CKα-5 may also be employed to inhibit T-cell proliferation by the inhibition of IL-2 biosynthesis for the treatment of T-cell mediated auto-immune diseases and lymphocytic leukemias. CKα-5 may also be employed to stimulate wound healing, both via the recruitment of debris clearing and connective tissue promoting inflammatory cells and also via its control of excessive TGF-mediated fibrosis. In this same manner, CKα-5 may also be employed to treat other fibrotic disorders, including liver cirrhosis, osteoarthritis and pulmonary fibrosis. CKα-5 also increases the presence of eosinophils which have the distinctive function of killing the larvae of parasites that invade tissues, as in schistosomiasis, trichinosis and ascariasis. It may also be employed to regulate hematopoiesis, by regulating the activation and differentiation of various hematopoietic progenitor cells, for example, to release mature leukocytes from the bone marrow following chemotherapy, i.e., in stem cell mobilization. CKα-5 may also be employed to treat sepsis. Also, by making a specific mutation to include an ELR motif, CKα-5-ELR will have angiogenic activities which are useful for treating all of the disease states where angiogenesis would be beneficial, i.e., to promote wound healing, re-vascularization of damaged limbs from injury or disease, and others known to those of skill in the art.

Formulations

The CKα-5 polypeptide composition will be formulated and dosed in a fashion consistent with good medical practice, taking into account the clinical condition of the individual patient (especially the side effects of treatment with CKα-5 polypeptide alone), the site of delivery of the CKα-5 polypeptide composition, the method of administration, the scheduling of administration, and other factors known to practitioners. The "effective amount" of CKα-5 polypeptide for purposes herein is thus determined by such considerations.

As a general proposition, the total pharmaceutically effective amount of CKα-5 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the CKα-5 polypeptide is typically administered at a dose rate of about 1 μg/kg/hour to about 50 μg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the CKα-5 of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The CKα-5 polypeptide is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547-556 (1983)), poly (2-hydroxyethyl methacrylate) (R. Langer et al., *J. Biomed. Mater. Res.* 15:167-277 (1981), and R. Langer, *Chem. Tech.* 12:98-105 (1982)), ethylene vinyl acetate (R. Langer et al., Id.) or poly-D-(−)-3-hydroxybutyric acid (EP 133,988). Sustained-release CKα-5 polypeptide compositions also include liposomally entrapped CKα-5 polypeptide. Liposomes containing CKα-5 polypeptide are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal CKα-5 polypeptide therapy.

For parenteral administration, in one embodiment, the CKα-5 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the CKα-5 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The CKα-5 polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of CKα-5 polypeptide salts.

CKα-5 polypeptide to be used for therapeutic administration must be sterile. Sterility is readily accomplished by filtration through sterile filtration membranes (e.g., 0.2 micron membranes). Therapeutic CKα-5 polypeptide compositions generally are placed into a container having a sterile access port, for example, an intravenous solution bag or vial having a stopper pierceable by a hypodermic injection needle.

CKα-5 polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous CKα-5 polypeptide solution, and the resulting mixture is lyophilized. The infusion solution is prepared by reconstituting the lyophilized CKα-5 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of CKα-5 on cells, such as its interaction with CKα-5-binding molecules such as receptor molecules. An agonist is a compound which increases the natural biological functions of CKα-5 or which functions in a manner similar to CKα-5, while antagonists decrease or eliminate such functions.

In another aspect of this embodiment the invention provides a method for identifying a receptor protein or other ligand-binding protein which binds specifically to a CKα-5 polypeptide. For example, a cellular compartment, such as a membrane or a preparation thereof, may be prepared from a cell that expresses a molecule that binds CKα-5. The preparation is incubated with labeled CKα-5 CKα-5 and complexes of CKα-5 bound to the receptor or other binding protein are isolated and characterized according to routine methods known in the art. Alternatively, the CKα-5 polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds CKα-5, such as a molecule of a signaling or regulatory pathway modulated by CKα-5. The preparation is incubated with labeled CKα-5 in the absence or the presence of a candidate molecule which may be a CKα-5 agonist or antagonist. The ability of the candidate molecule to bind the binding molecule is reflected in decreased binding of the labeled ligand. Molecules which bind gratuitously, i.e., without inducing the effects of CKα-5 on binding the CKα-5 binding molecule, are most likely to be good antagonists. Molecules that bind well and elicit effects that are the same as or closely related to CKα-5 are agonists.

CKα-5-like effects of potential agonists and antagonists may by measured, for instance, by determining activity of a second messenger system following interaction of the candidate molecule with a cell or appropriate cell preparation, and comparing the effect with that of CKα-5 or molecules that elicit the same effects as CKα-5. Second messenger systems that may be useful in this regard include but are not limited to AMP guanylate cyclase, ion channel or phosphoinositide hydrolysis second messenger systems.

Another example of an assay for CKα-5 antagonists is a competitive assay that combines CKα-5 and a potential antagonist with membrane-bound CKα-5 receptor molecules or recombinant CKα-5 receptor molecules under appropriate conditions for a competitive inhibition assay. CKα-5 can be labeled, such as by radioactivity, such that the number of CKα-5 molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing CKα-5-induced activities, thereby preventing the action of CKα-5 by excluding CKα-5 from binding.

Other potential antagonists include antisense molecules. Antisense technology can be used to control gene expression through antisense DNA or RNA or through triple-helix formation. Antisense techniques are discussed, for example, in Okano, *J. Neurochem.* 56: 560 (1991); "Oligodeoxynucleotides as Antisense Inhibitors of Gene Expression." CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of CKα-5. The antisense RNA oligonucleotide hybridizes to the mRNA in vivo and blocks translation of the mRNA molecule into CKα-5 polypeptide. The oligonucleotides described above can also be delivered to cells such that the antisense RNA or DNA may be expressed in vivo to inhibit production of CKα-5 protein.

The agonists and antagonists may be employed in a composition with a pharmaceutically acceptable carrier, e.g., as described above.

The antagonists may be employed for instance to inhibit the chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by preventing the recruitment and activation of mononuclear phagocytes. They may also be employed to treat idiopathic hypereosinophilic syndrome by preventing eosinophil production and migration. Endotoxic shock may also be treated by the antagonists by preventing the migration of macrophages and their production of the human chemokine polypeptides of the present invention. The antagonists may also be employed for treating atherosclerosis, by preventing monocyte infiltration in the artery wall. The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines. The antagonists may also be employed to treat cases of bone marrow failure, for example, aplastic anemia and myelodysplastic syndrome. The antagonists may also be employed to treat asthma and allergy by preventing eosinophil accumulation in the lung. The antagonists may also be employed to treat subepithelial basement membrane fibrosis which is a prominent feature of the asthmatic lung. Antibodies against CKα-5 may be employed to bind to and inhibit CKα-5 activity to treat ARDS, by preventing infiltration of neutrophils into the lung after injury. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a CKα-5 protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1(a)

Expression and Purification of "His-tagged" CKα-5 in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the carboxyl terminus of that polypeptide.

The DNA sequence encoding the desired portion CKα-5 protein lacking the hydrophobic leader sequence and transmembrane domain is amplified from the deposited cDNA clone using PCR oligonucleotide primers which anneal to the amino terminal sequences of the desired portion of the CKα-5 protein and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5' primer has the sequence 5' GCGCCATGGAATGGCAACGAGGGCAGC 3' (SEQ ID NO: 15) containing the underlined NcoI restriction site. One of ordinary skill in the art would appreciate, of course, that the point in the protein coding sequence where the 5' primer begins may be varied to amplify a DNA segment encoding any desired portion of the complete protein shorter or longer than the mature form. The 3' primer has the sequence 5' CGC AAGCTTTTATGTGGCTGATGTCCTGGC 3' (SEQ ID NO: 16) containing the underlined HindIII restriction.

The amplified CKα-5 DNA fragment and the vector pQE60 are digested with NcoI and HindIII and the digested DNAs are then ligated together. Insertion of the CKα-5 DNA into the restricted pQE60 vector places the CKα-5 protein coding region downstream from the IPTG-inducible promoter and in-frame with an initiating AUG and the six histidine codons.

Alternatively, a preferred bacterial expression vector "pHE4-5" containing an ampicillin resistance gene may be used in this example. pHE4-5/MPIFD23 vector plasmid DNA contains a filler insert between unique restriction enzyme sites NdeI and Asp718 and was deposited with the American Type Culture Collection, 12301 Park Lawn Drive, Rockville, Md. 20852, on Sep. 30, 1997 and given Accession No. 209311. Using 5' and 3' primers described herein with restriction enzyme sites for NdeI and Asp 718 substituted for the NcoI and HindIII sites in the respective primers, a suitable CKα-5 encoding DNA fragment for subcloning into pHE4-5 can be amplified. The stuffer DNA insert in pHE4-5/MPIFD23 should be removed prior to ligating the CKα-5 fragment to pHE4-5. pHE4-5 contains a strong bacterial promoter allowing for high yields of most heterologous proteins.

The ligation mixture is transformed into competent *E. coli* cells using standard procedures such as those described in Sambrook et al., *Molecular Cloning: a Laboratory Manual*, 2*nd* Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing CKα-5 protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3-4 hours at 4° C. in 6M guanidine-HCl, pH 8. The cell debris is removed by centrifugation, and the supernatant containing the CKα-5 is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the CKα-5 is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The following alternative method may be used to purify CKα-5 expressed in *E coli* when it is present in the form of inclusion bodies. Unless otherwise specified, all of the following steps are conducted at 4-10° C.

Upon completion of the production phase of the *E. coli* fermentation, the cell culture is cooled to 4-10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GUHCl) for 2-4 hours. After 7000×g centrifugation for 15 min., the pellet is discarded and the CKα-5 polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded CKα-5 polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the CKα-5 polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the CKα-5 polypeptide (determined, for instance, by 16% SDS-PAGE) are then pooled.

The resultant CKα-5 polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2

Cloning and Expression of CKα-5 protein in a Baculovirus Expression System

In this illustrative example, the plasmid shuttle vector pA2 is used to insert the cloned DNA encoding complete protein, including its naturally associated secretory signal (leader) sequence, into a baculovirus to express the mature CKα-5 protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39 (1989).

The cDNA sequence encoding the full length CKα-5 protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5' CGC <u>GGATCC</u>GCCATCATGGGACGGGACTTGCGG 3' (SEQ ID NO: 17) containing the underlined BamHI restriction enzyme site, an efficient signal for initiation of translation in eukaryotic cells, as described by Kozak, M., *J. Mol. Biol.* 196:947-950 (1987). The 3' primer has the sequence 5' GCG <u>TCTAGA</u>TCAGGTATTAGAGTCAGG 3' (SEQ ID NO:18) containing the underlined XbaI restriction site. Those of ordinary skill in the art will recognize that other primers could be used to generate nucleic acid fragments encoding shorter polypeptides. For example, the 5' primer above (SEQ ID NO:17) with the following 3' primer could be used to amplify the nucleic acid fragment encoding the soluble extracellular domain:

5' GCG<u>TCTAGA</u>TTATGTGGCTGATGTCCTGGC 3' (SEQ ID NO: 19). The 3' primer contains the underlined XbaI site.

The amplified fragment is isolated from a 1% agarose gel using a commercially available kit ("Geneclean," BIO 101 Inc., La Jolla, Calif.). The fragment then is digested with BamHI and XbaI and again is purified on a 1% agarose gel.

The plasmid is digested with the restriction enzymes BamHI and XbaI and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

Fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human CKα-5 gene by digesting DNA from individual colonies using BamHI and XbaI and then analyzing the digestion product by gel electrophoresis. The sequence of the cloned fragment is confirmed by DNA sequencing. This plasmid is designated herein pA2GPCKα-5.

Five μg of the plasmid pA2GPCKα-5 is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413-7417 (1987). One μg of BaculoGold™ virus DNA and 5 μg of the plasmid pA2GPCKα-5 are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC® CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-CKα-5.

To verify the expression of the CKα-5 gene Sf9 cells are grown in Grace's medium supplemented with 10% heat-inactivated FBS. The cells are infected with the recombinant baculovirus V-CKα-5 at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form or extracellular domain of the CKα-5 protein and thus the cleavage point and length of the naturally associated secretory signal peptide.

Example 3

Cloning and Expression of CKα-5 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC® 37152), pSV2dhfr (ATCC® 37146) and pBC12MI (ATCC® 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., Biochem J. 227:277-279 (1991); Bebbington et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pCKα-5HA, is made by cloning a portion of the cDNA encoding the extracellular domain of the CKα-5 protein into the expression vector pcDNAI/Amp or pcDNAIII (which can be obtained from Invitrogen, Inc.).

The expression vector pcDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., Cell 37: 767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the soluble extracellular domain of the CKα-5 polypeptide is cloned into the polylinker region of the vector so that recombinant protein expression is directed by the CMV promoter. The plasmid construction strategy is as follows. The CKα-5 cDNA of the deposited clone is amplified using primers that contain convenient restriction sites, much as described above for construction of vectors for expression of CKα-5 in E. coli. Suitable primers include the following, which are used in this example. The 5' primer, containing the underlined BamHI site, a Kozak sequence, and an AUG start codon, has the following sequence: 5' CGC GGATCCGCCATCATGGGACGGGACTTGCGG 3' (SEQ ID NO:17). The 3' primer, containing the underlined XbaI site has the following sequence: 5' GCG TCTAGATCAGGTATTAGAGTCAGG 3' (SEQ ID NO: 18).

The PCR amplified DNA fragment and the vector, pcD-NAI/Amp, are digested with BamHI and XbaI and then ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the extracellular domain of the CKα-5 polypeptide For expression of recombinant CKα-5, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of CKα-5 by the vector.

Expression of the CKα-5-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of CKα-5 polypeptide in this example. Plasmid pC4 is a derivative of the plasmid pSV2-dhfr (ATCC® Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357-1370, Hamlin, J. L. and Ma, C. 1990, *Biochem. et Biophys. Acta,* 1097:107-143, Page, M. J. and Sydenham, M. A. 1991, *Biotechnology* 9:64-68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438-447) plus a fragment isolated from the enhancer of the immediate early gene of human cytomegalovirus (CMV) (Boshart et al., *Cell* 41:521-530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the CKα-5 polypeptide in a regulated way in mammalian cells (Gossen, M., & Bujard, H. 1992, *Proc. Natl. Acad. Sci. USA* 89:5547-5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and XbaI and then dephosphorylated using calf intestinal phosphatase by procedures known in the art. The vector is then isolated from a 1% agarose gel.

The DNA sequence encoding the extracellular domain of the CKα-5 polypeptide is amplified using PCR oligonucleotide primers corresponding to the 5' and 3' sequences of the desired portion of the gene. The 5' and 3' primers are the same as those used in Example 3(a) above.

The amplified fragment is digested with the endonucleases BamHI and XbaI and then purified again on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100-200 μM. Expression of the desired gene product is analyzed, for instance, by SDS-PAGE and Western blot or by reversed phase HPLC analysis.

Example 4

Tissue Distribution of CKα-5 mRNA Expression

Northern blot analysis is carried out to examine CKα-5 gene expression in human tissues, using methods described by, among others, Sambrook et al., cited above. A cDNA probe containing the entire nucleotide sequence of the CKα-5 protein (SEQ ID NO:1) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for CKα-5 mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the sequence listing in both hard copy and electronic form submitted herewith is incorporated herein by reference.

---

What is claimed is:

1. An isolated antibody or fragment thereof that specifically binds to a protein selected from the group consisting of:
   (a) a protein whose amino acid sequence consists of amino acid residues 1 to 254 of SEQ ID NO:2;
   (b) a protein whose amino acid sequence consists of amino acid residues 28 to 254 of SEQ ID NO:2;
   (c) a protein whose amino acid sequence consists of amino acid residues 28 to 205 of SEQ ID NO:2;
   (d) a protein whose amino acid sequence consists of a portion of SEQ ID NO:2, wherein said portion is at least 30 contiguous amino acid residues in length; and
   (e) a protein whose amino acid sequence consists of a portion of SEQ ID NO:2, wherein said portion is at least 50 contiguous amino acid residues in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 1 that specifically binds protein (e).

7. The antibody or fragment thereof of claim 2 that specifically binds protein (b).

8. The antibody or fragment thereof of claim 3 wherein said protein bound by said antibody or fragment thereof is glycosylated.

9. The antibody or fragment thereof of claim 3 wherein said antibody or fragment thereof is polyclonal.

10. The antibody or fragment thereof of claim 3 wherein said antibody or fragment thereof is monoclonal.

11. The antibody or fragment thereof of claim 3 which is selected from the group consisting of:
   (a) a chimeric antibody or fragment thereof;
   (b) a single chain antibody; and
   (c) a Fab fragment; and
   (d) a F(ab')2 fragment.

12. The antibody or fragment thereof of claim 3 which is labeled.

13. The antibody or fragment thereof of claim 3 wherein said antibody or fragment thereof specifically binds to said protein in a Western blot or an ELISA.

14. An isolated cell that produces the antibody or fragment thereof of claim 3.

15. A hybridoma that produces the antibody or fragment thereof of claim 3.

16. A method of detecting CKα-5 protein in a biological sample comprising:
   (a) contacting the biological sample with the antibody or fragment thereof of claim 3; and
   (b) detecting the CKα-5 protein in the biological sample.

17. An isolated antibody or fragment thereof that specifically binds a CKα-5 protein expressed from a cell wherein said CKα-5 protein is encoded by a polynucleotide encoding amino acids 1 to 254 of SEQ ID NO:2.

18. The antibody or fragment thereof of claim 17 wherein said antibody or fragment thereof is monoclonal.

19. The antibody or fragment thereof of claim 17 wherein said antibody or fragment thereof is polyclonal.

20. The antibody or fragment thereof of claim 17 which is selected from the group consisting of:
   (a) a chimeric antibody or fragment thereof;
   (b) a single chain antibody; and
   (c) a Fab fragment; and
   (d) a F(ab')2 fragment.

21. The antibody or fragment thereof of claim 17 wherein said antibody or fragment thereof specifically binds to said protein in a Western blot or an ELISA.

22. The antibody or fragment thereof of claim 17 wherein the amino acid sequence of said CKα-5 protein consists of amino acid residues 28 to 205 of SEQ ID NO:2.

23. An isolated antibody or fragment thereof that specifically binds a CKα-5 protein purified from a cell culture wherein said CKα-5 protein is encoded by a polynucleotide encoding amino acids 1 to 254 of SEQ ID NO:2.

24. The antibody or fragment thereof of claim 23 wherein said antibody or fragment thereof is monoclonal.

25. The antibody or fragment thereof of claim 23 wherein said antibody or fragment thereof is polyclonal.

26. The antibody or fragment thereof of claim 23 which is selected from the group consisting of:
   (a) a chimeric antibody or fragment thereof;
   (b) a single chain antibody; and (c) a Fab fragment; and (d) a F(ab')2 fragment.

27. The antibody or fragment thereof of claim 23 wherein said antibody or fragment thereof specifically binds to said protein in a Western blot or an ELISA.

28. The antibody or fragment thereof of claim 23 wherein the amino acid sequence of said CKα-5 protein consists of amino acid residues 28 to 205 of SEQ ID NO:2.

* * * * *